United States Patent
Fallin et al.

(10) Patent No.: US 10,376,367 B2
(45) Date of Patent: Aug. 13, 2019

(54) ORTHOPEDIC FASTENERS, INSTRUMENTS AND METHODS

(71) Applicant: First Ray, LLC, Logan, UT (US)

(72) Inventors: T. Wade Fallin, Hyde Park, UT (US); Daniel John Triplett, Providence, UT (US)

(73) Assignee: First Ray, LLC, Logan, UT (US)

( * ) Notice: Subject to any disclaimer, the term of this patent is extended or adjusted under 35 U.S.C. 154(b) by 314 days.

(21) Appl. No.: 15/194,016

(22) Filed: Jun. 27, 2016

(65) Prior Publication Data
US 2017/0000537 A1    Jan. 5, 2017

Related U.S. Application Data

(60) Provisional application No. 62/188,185, filed on Jul. 2, 2015, provisional application No. 62/308,011, filed on Mar. 14, 2016.

(51) Int. Cl.
| | |
|---|---|
| A61B 17/064 | (2006.01) |
| A61F 2/30 | (2006.01) |
| A61B 17/88 | (2006.01) |
| A61B 17/70 | (2006.01) |
| A61B 17/80 | (2006.01) |
| A61F 2/38 | (2006.01) |
| A61B 17/68 | (2006.01) |
| A61B 17/15 | (2006.01) |
| A61B 17/17 | (2006.01) |

(52) U.S. Cl.
CPC .......... *A61F 2/30724* (2013.01); *A61B 17/68* (2013.01); *A61B 17/7059* (2013.01); *A61B 17/8004* (2013.01); *A61B 17/808* (2013.01); *A61B 17/809* (2013.01); *A61B 17/8061* (2013.01); *A61B 17/8095* (2013.01); *A61B 17/8872* (2013.01); *A61F 2/30749* (2013.01); *A61F 2/389* (2013.01); *A61F 2/3859* (2013.01); *A61B 17/0642* (2013.01); *A61B 17/15* (2013.01); *A61B 17/151* (2013.01); *A61B 17/17* (2013.01); *A61B 2017/681* (2013.01); *A61F 2002/30884* (2013.01)

(58) Field of Classification Search
CPC .................................................. A61B 17/0642
See application file for complete search history.

(56) References Cited

U.S. PATENT DOCUMENTS

| | | |
|---|---|---|
| 2,133,859 A | 10/1938 | Hawley |
| 2,485,531 A | 10/1949 | Dzus |

(Continued)

FOREIGN PATENT DOCUMENTS

| | | |
|---|---|---|
| EP | 1679044 A2 | 7/2006 |
| EP | 1952776 A1 | 8/2008 |

(Continued)

OTHER PUBLICATIONS

US 9,125,700 B2, 09/2015, Gonzalez-Hernandez (withdrawn)

(Continued)

*Primary Examiner* — Nicholas W Woodall
(74) *Attorney, Agent, or Firm* — David Meibos; Maywood IP Law

(57) ABSTRACT

Examples of the invention relate to methods, implants, and instruments for compressing first and second bone portions or a bone portion and an implant together.

18 Claims, 23 Drawing Sheets

(56) References Cited

U.S. PATENT DOCUMENTS

| | | |
|---|---|---|
| 2,489,870 A | 11/1949 | Dzus |
| 2,511,051 A | 6/1950 | Dzus |
| 2,760,488 A | 8/1956 | Pierce |
| 2,825,329 A | 3/1958 | Caesar |
| 3,618,447 A | 11/1971 | Goins |
| 3,709,218 A | 1/1973 | Halloran |
| 3,939,828 A | 2/1976 | Mohr |
| 4,047,524 A | 9/1977 | Hall |
| 4,060,089 A | 11/1977 | Noiles |
| 4,456,005 A | 6/1984 | Lichty |
| 4,635,637 A | 1/1987 | Schreiber |
| 4,688,561 A | 8/1987 | Reese |
| 4,696,300 A | 9/1987 | Anderson |
| 4,736,746 A | 4/1988 | Anderson |
| 4,838,254 A | 6/1989 | Gauthier |
| 4,841,960 A | 6/1989 | Garner |
| 4,994,073 A | 2/1991 | Green |
| 5,053,038 A | 10/1991 | Sheehan |
| 5,085,661 A | 2/1992 | Moss |
| 5,250,049 A | 10/1993 | Michael |
| 5,269,783 A | 12/1993 | Sander |
| 5,293,881 A | 3/1994 | Green |
| 5,312,412 A | 5/1994 | Whipple |
| 5,314,429 A | 5/1994 | Goble |
| 5,330,468 A | 7/1994 | Burkhart |
| 5,336,240 A | 8/1994 | Metzler |
| 5,341,622 A | 8/1994 | Odermatt |
| 5,344,005 A | 9/1994 | Kettner |
| 5,350,060 A | 9/1994 | Alpern |
| 5,350,380 A | 9/1994 | Goble |
| 5,354,300 A | 10/1994 | Goble |
| 5,358,624 A | 10/1994 | Roshdy |
| 5,374,268 A | 12/1994 | Sander |
| 5,383,367 A | 1/1995 | Goble |
| 5,601,571 A | 2/1997 | Moss |
| 5,643,319 A | 7/1997 | Green |
| 5,658,313 A | 8/1997 | Thal |
| 5,665,112 A | 9/1997 | Thal |
| 5,674,247 A | 10/1997 | Sohn |
| 5,728,136 A | 3/1998 | Thal |
| 5,810,822 A | 9/1998 | Mortier |
| 5,873,891 A | 2/1999 | Sohn |
| 5,891,168 A | 4/1999 | Thal |
| 5,919,194 A | 7/1999 | Anderson |
| 5,921,986 A | 7/1999 | Bonutti |
| 5,954,747 A | 9/1999 | Clark |
| 6,001,101 A | 12/1999 | Augagneur |
| 6,030,162 A | 2/2000 | Huebner |
| 6,117,160 A | 9/2000 | Bonutti |
| 6,149,669 A | 11/2000 | Li |
| 6,179,839 B1 | 1/2001 | Weiss |
| 6,190,401 B1 | 2/2001 | Green |
| 6,203,545 B1 | 3/2001 | Stofella |
| 6,248,109 B1 | 6/2001 | Stofella |
| 6,258,091 B1 | 7/2001 | Sevrain |
| 6,277,130 B1 | 8/2001 | Shadduck |
| 6,302,887 B1 | 10/2001 | Spranza |
| 6,306,159 B1 | 10/2001 | Schwartz |
| 6,364,884 B1 | 4/2002 | Bowman |
| 6,402,766 B2 | 6/2002 | Bowman |
| 6,423,073 B2 | 7/2002 | Bowman |
| 6,436,110 B2 | 8/2002 | Bowman |
| 6,447,517 B1 | 9/2002 | Bowman |
| 6,497,707 B1 | 12/2002 | Bowman |
| 6,533,802 B2 | 3/2003 | Bojarksi |
| 6,554,852 B1 | 4/2003 | Oberlander |
| 6,589,244 B1 | 7/2003 | Sevrain |
| 6,635,073 B2 | 10/2003 | Bonutti |
| 6,669,698 B1 | 12/2003 | Tromanhauser |
| 6,689,136 B2 | 11/2004 | Stoffella |
| 6,818,010 B2 | 11/2004 | Eichhorn |
| 6,921,401 B2 | 7/2005 | Lerch |
| 6,942,668 B2 | 9/2005 | Padget |
| 6,972,027 B2 | 12/2005 | Fallin |
| 7,008,428 B2 | 3/2006 | Cachia |
| 7,060,068 B2 | 6/2006 | Tromanhauser |
| 7,087,073 B2 | 8/2006 | Bonutti |
| 7,153,309 B2 | 12/2006 | Huebner |
| 7,214,232 B2 | 5/2007 | Bowman |
| 7,326,213 B2 | 2/2008 | Benderev |
| 7,344,538 B2 | 3/2008 | Myerson |
| 7,468,074 B2 | 12/2008 | Caborn |
| 7,491,220 B2 | 2/2009 | Coughln |
| 7,563,275 B2 | 7/2009 | Falahee |
| 7,578,825 B2 | 8/2009 | Huebner |
| 7,582,107 B2 | 9/2009 | Trail |
| 7,588,594 B2 | 9/2009 | Sander |
| 7,603,192 B2 | 10/2009 | Martin |
| 7,608,094 B2 | 10/2009 | Falahee |
| 7,625,395 B2 | 12/2009 | Muckter |
| 7,708,738 B2 | 5/2010 | Fourcault |
| 7,771,457 B2 | 8/2010 | Kay |
| 7,785,355 B2 | 8/2010 | Mohr |
| 7,837,717 B2 | 11/2010 | Deffenbaugh |
| 7,875,063 B1 | 1/2011 | Sander |
| 7,931,680 B2 | 4/2011 | Myerson |
| 7,950,559 B2 | 5/2011 | Peterson |
| 7,951,198 B2 | 5/2011 | Sucec |
| 8,002,812 B2 | 8/2011 | Falahee |
| 8,012,080 B2 | 9/2011 | Chu |
| 8,016,867 B2 | 9/2011 | Bowman |
| 8,034,076 B2 | 10/2011 | Criscuolo |
| 8,062,297 B2 | 11/2011 | Faillace |
| 8,062,301 B2 | 11/2011 | Ammann |
| 8,097,007 B2 | 1/2012 | Evans |
| 8,100,939 B2 | 1/2012 | Peterson |
| 8,100,954 B2 | 1/2012 | Kay |
| 8,114,101 B2 | 2/2012 | Criscuolo |
| 8,118,836 B2 | 2/2012 | Denham |
| 8,118,848 B2 | 2/2012 | Ducharme |
| 8,133,283 B2 | 3/2012 | Wilson |
| 8,137,382 B2 | 3/2012 | Denham |
| 8,162,996 B2 | 4/2012 | Schelling |
| 8,167,918 B2 | 5/2012 | Strnad |
| 8,187,308 B2 | 5/2012 | Mullaney |
| 8,206,400 B2 | 6/2012 | Falahee |
| 8,231,627 B2 | 7/2012 | Huebner |
| 8,235,995 B2 | 8/2012 | Focht |
| 8,257,403 B2 | 9/2012 | Den Hartog |
| 8,257,406 B2 | 9/2012 | Kay |
| 8,262,706 B2 | 9/2012 | Olms |
| 8,292,898 B2 | 10/2012 | Castaneda |
| 8,313,492 B2 | 11/2012 | Wong |
| 8,313,517 B2 | 11/2012 | Mohr |
| 8,337,537 B2 | 12/2012 | Pelo |
| 8,348,980 B2 | 1/2013 | Prasad |
| 8,357,186 B2 | 1/2013 | Hadi |
| 8,361,113 B2 | 1/2013 | Stone |
| 8,382,807 B2 | 2/2013 | Austin |
| 8,419,745 B2 | 4/2013 | Sixto |
| 8,425,574 B2 | 4/2013 | Huebner |
| 8,449,561 B2 | 5/2013 | Bowman |
| 8,518,088 B2 | 8/2013 | Castaneda |
| 8,535,355 B2 | 9/2013 | Prasad |
| 8,551,107 B2 | 10/2013 | Ng |
| 8,574,266 B2 | 11/2013 | Falahee |
| 8,585,742 B2 | 11/2013 | Windolf |
| 8,585,744 B2 | 11/2013 | Duggal |
| 8,591,545 B2 | 11/2013 | Lunn |
| 8,597,300 B2 | 12/2013 | Deffenbaugh |
| 8,597,311 B2 | 12/2013 | Criscuolo |
| 8,617,227 B2 | 12/2013 | Sucec |
| 8,652,136 B2 | 2/2014 | Yang |
| 8,652,171 B2 | 2/2014 | Stone |
| 8,657,820 B2 | 2/2014 | Kubiak |
| 8,668,718 B2 | 3/2014 | Euteneuer |
| 8,679,123 B2 | 3/2014 | Kinmon |
| 8,728,102 B2 | 5/2014 | Criscuolo |
| 8,734,492 B2 | 5/2014 | Mohr |
| 8,747,408 B2 | 6/2014 | Falahee |
| 8,758,414 B2 | 6/2014 | Ng |
| 8,763,878 B2 | 7/2014 | Euteneuer |
| 8,764,763 B2 | 7/2014 | Wong |
| 8,778,000 B2 | 7/2014 | Haddad |

(56) References Cited

U.S. PATENT DOCUMENTS

| | | |
|---|---|---|
| 8,789,736 B2 | 7/2014 | Dudai |
| 8,790,368 B2 | 7/2014 | Sullivan |
| 8,808,336 B2 | 8/2014 | Duggal |
| 8,821,536 B2 | 9/2014 | Euteneuer |
| 8,821,537 B2 | 9/2014 | Euteneuer |
| 8,834,534 B2 | 9/2014 | Impellizzeri |
| 8,840,642 B2 | 9/2014 | Euteneuer |
| 8,845,725 B2 | 9/2014 | Barwood |
| 8,920,464 B2 | 12/2014 | Euteneuer |
| 8,926,495 B2 | 1/2015 | Chu |
| 8,940,016 B2 | 1/2015 | Peterson |
| 8,951,287 B1 | 2/2015 | Green |
| 8,998,969 B2 | 4/2015 | Deffenbaugh |
| 9,011,501 B2 | 4/2015 | Mikhail |
| 9,027,819 B2 | 5/2015 | Euteneuer |
| 9,033,201 B2 | 5/2015 | Euteneuer |
| 9,095,337 B2 | 8/2015 | Euteneuer |
| 9,095,338 B2 | 8/2015 | Taylor |
| 9,107,745 B2 | 8/2015 | Bouduban |
| 9,433,452 B2 | 9/2016 | Weiner |
| 9,463,012 B2 | 10/2016 | Bonutti |
| 2002/0019649 A1 | 2/2002 | Sikora |
| 2002/0052628 A1 | 5/2002 | Bowman |
| 2002/0095157 A1 | 7/2002 | Bowman |
| 2002/0169452 A1 | 11/2002 | Tormala |
| 2003/0032961 A1 | 2/2003 | Pelo |
| 2003/0045881 A1 | 3/2003 | Barouk |
| 2003/0105464 A1 | 6/2003 | Schreurs |
| 2003/0125743 A1 | 7/2003 | Roman |
| 2003/0143918 A1 | 8/2003 | Putnam |
| 2003/0167072 A1 | 9/2003 | Oberlander |
| 2003/0171754 A1 | 9/2003 | Del Medico |
| 2004/0015171 A1 | 1/2004 | Bojarski |
| 2004/0092937 A1 | 5/2004 | Criscuolo |
| 2004/0127908 A1 | 7/2004 | Roman |
| 2004/0138664 A1 | 7/2004 | Bowman |
| 2004/0138683 A1 | 7/2004 | Shelton |
| 2004/0138705 A1 | 7/2004 | Heino |
| 2004/0210234 A1 | 10/2004 | Coillard |
| 2005/0033302 A1 | 2/2005 | Frank |
| 2005/0085819 A1 | 4/2005 | Ellis |
| 2005/0143734 A1 | 6/2005 | Cachia |
| 2005/0159762 A1 | 7/2005 | Nuutinen |
| 2006/0015102 A1 | 1/2006 | Toullec |
| 2006/0058802 A1* | 3/2006 | Kofoed ............... A61B 17/0642 606/75 |
| 2006/0195103 A1 | 8/2006 | Padget |
| 2006/0241608 A1 | 10/2006 | Myerson |
| 2007/0005071 A1 | 1/2007 | Kucklick |
| 2007/0014649 A1 | 1/2007 | James |
| 2007/0088362 A1 | 4/2007 | Bonutti |
| 2007/0142838 A1 | 6/2007 | Jordan |
| 2007/0156175 A1 | 7/2007 | Weadock |
| 2007/0276388 A1 | 11/2007 | Robertson |
| 2008/0093839 A1 | 4/2008 | Flynn et al. |
| 2008/0131544 A1 | 6/2008 | Sander |
| 2008/0161808 A1 | 7/2008 | Fox |
| 2008/0161850 A1 | 7/2008 | Weisenburgh |
| 2008/0287991 A1 | 11/2008 | Fromm |
| 2009/0036931 A1 | 2/2009 | Pech |
| 2009/0093849 A1 | 4/2009 | Grabowski |
| 2009/0149884 A1 | 6/2009 | Snyder |
| 2009/0177203 A1 | 7/2009 | Reiley |
| 2009/0254090 A1 | 10/2009 | Lizee |
| 2009/0287259 A1 | 11/2009 | Trenhaile |
| 2009/0306723 A1 | 12/2009 | Anapliotis |
| 2009/0312802 A1 | 12/2009 | DaSilva |
| 2009/0318980 A1 | 12/2009 | Falahee |
| 2010/0016966 A1 | 1/2010 | Sander |
| 2010/0036430 A1 | 2/2010 | Hartdegen |
| 2010/0076487 A1 | 2/2010 | Ilahi |
| 2010/0087859 A1 | 4/2010 | Jackson, Jr. |
| 2010/0106194 A1 | 4/2010 | Bonutti |
| 2010/0191332 A1 | 7/2010 | Euteneuer |
| 2010/0241227 A1 | 9/2010 | Euteneuer |
| 2010/0256687 A1 | 10/2010 | Neufeld |
| 2011/0004221 A1 | 1/2011 | Euteneuer |
| 2011/0009866 A1 | 1/2011 | Johnson |
| 2011/0087326 A1 | 4/2011 | Paulos |
| 2011/0112558 A1 | 5/2011 | Whayne |
| 2011/0137356 A1 | 6/2011 | Kollmer |
| 2011/0224734 A1 | 9/2011 | Schelling |
| 2011/0270278 A1 | 11/2011 | Overes |
| 2011/0295324 A1 | 12/2011 | Donley |
| 2012/0035613 A1 | 2/2012 | Falahee |
| 2012/0059397 A1 | 3/2012 | Criscuolo |
| 2012/0071566 A1 | 3/2012 | Kelly |
| 2012/0071935 A1 | 3/2012 | Keith |
| 2012/0109157 A1 | 5/2012 | Criscuolo |
| 2012/0109215 A1 | 5/2012 | Ducharme |
| 2012/0130374 A1 | 5/2012 | Bouduban |
| 2012/0172936 A1 | 7/2012 | Horrell |
| 2012/0184959 A1 | 7/2012 | Price |
| 2012/0209334 A1 | 8/2012 | Lewis |
| 2012/0245643 A1 | 9/2012 | Impellizzeri |
| 2012/0277802 A1 | 11/2012 | Olms |
| 2012/0303033 A1 | 11/2012 | Weiner |
| 2013/0096559 A1 | 4/2013 | Katrana |
| 2013/0123863 A1 | 5/2013 | Hollis |
| 2013/0138154 A1 | 5/2013 | Reiley |
| 2013/0153627 A1 | 6/2013 | Euteneuer |
| 2013/0153628 A1 | 6/2013 | Euteneuer |
| 2013/0158661 A1 | 6/2013 | Euteneuer |
| 2013/0165972 A1 | 6/2013 | Sullivan |
| 2013/0172889 A1 | 7/2013 | Tyber |
| 2013/0172942 A1 | 7/2013 | Lewis |
| 2013/0226248 A1 | 8/2013 | Hatch |
| 2013/0226252 A1 | 8/2013 | Mayer |
| 2013/0231667 A1 | 9/2013 | Taylor |
| 2013/0240598 A1 | 9/2013 | Euteneuer |
| 2013/0261670 A1 | 10/2013 | Laeng |
| 2013/0261677 A1 | 10/2013 | Bouduban |
| 2013/0267956 A1* | 10/2013 | Terrill ............... A61B 17/0642 606/75 |
| 2013/0274769 A1 | 10/2013 | Bonutti |
| 2014/0018809 A1 | 1/2014 | Allen |
| 2014/0025112 A1 | 1/2014 | Bonutti |
| 2014/0039561 A1 | 2/2014 | Weiner |
| 2014/0066984 A1 | 3/2014 | Falahee |
| 2014/0066995 A1 | 3/2014 | McCormick |
| 2014/0066996 A1 | 3/2014 | Price |
| 2014/0081327 A1 | 3/2014 | Lunn |
| 2014/0097228 A1 | 4/2014 | Taylor |
| 2014/0148859 A1 | 5/2014 | Taylor |
| 2014/0194927 A1 | 7/2014 | Kaiser |
| 2014/0249537 A1 | 9/2014 | Wong |
| 2014/0309639 A1 | 10/2014 | Averous |
| 2015/0080967 A1 | 3/2015 | DaSilva |
| 2015/0112370 A1 | 4/2015 | Euteneuer |
| 2015/0164564 A1 | 6/2015 | Reiley |
| 2016/0089138 A1 | 3/2016 | Early |
| 2016/0113770 A1 | 4/2016 | Early |
| 2016/0192930 A1 | 7/2016 | Finley |
| 2016/0242830 A1 | 8/2016 | Terrill |
| 2017/0252036 A1* | 9/2017 | Palmer ................ A61B 17/10 |

FOREIGN PATENT DOCUMENTS

| | | |
|---|---|---|
| EP | 1707138 B1 | 5/2009 |
| EP | 1927322 B1 | 6/2010 |
| EP | 1707140 B1 | 9/2011 |
| EP | 2606843 A1 | 6/2013 |
| FR | 376911 A | 8/1907 |
| FR | 551418 A | 4/1923 |
| FR | 2928824 A1 | 9/2009 |
| WO | 1998037825 A1 | 9/1998 |
| WO | 2003075775 A1 | 9/2003 |
| WO | 2007103333 A2 | 9/2007 |
| WO | 2008149308 A1 | 12/2008 |
| WO | 2010094846 A1 | 8/2010 |
| WO | 2010098820 A1 | 9/2010 |
| WO | 2010098909 A1 | 9/2010 |
| WO | 2010129156 A1 | 11/2010 |
| WO | 2012033928 A1 | 3/2012 |

(56) References Cited

FOREIGN PATENT DOCUMENTS

| | | |
|---|---|---|
| WO | 2012040862 A1 | 4/2012 |
| WO | 2013006833 A1 | 1/2013 |
| WO | 2013029600 A1 | 3/2013 |
| WO | 2013131974 A1 | 9/2013 |
| WO | 2013156545 A1 | 10/2013 |
| WO | 2014084974 A1 | 6/2014 |
| WO | 2014087111 A1 | 6/2014 |
| WO | 2014127294 A1 | 8/2014 |
| WO | 2016134160 A1 | 8/2016 |

OTHER PUBLICATIONS

The Next Generation in Foot & Ankle Repair and Reconstruction Technology 2016, Arthrex, Inc., www.arthrex.com, 2016, 76 pp.
Speed Continuous Active Compression Implant, A120-031 Rev. 2, BioMedical Enterprises, www.bme-tx.com, 2014, 2 pp.
Lower Extremity Congruent Plating System, Acumed, www.acumed.net, Nov. 2008, 20 pp.
Acutrak Headless Compression Screw, Acumed, www.acumed.net, Apr. 2012, 20 pp.
Acumed Forefoot/Midfoot Plating System Surgical Technique, Acumed, LLC, www.acumed.net, 2014, 28 pp.
Acumed Locking Forefoot/Midfoot Plating System, Acumed, www.acumed.net, Sep. 2010, 20 pp.
Comprehensive Foot System, Arthrex, Inc., www.arthrex.com, 2013, 6 pp.
Comprehensive Solutions for Forefoot and Midfoot Surgery Using the Mini TightRope System, Athrex, Inc., www.arthrex.com, 2012, 15 pp.
Compression FT Screw System, Athrex, Inc., www.arthrex.com, 2014, 6 pp.
Distal Extremities Orthopaedic Update, Arthrex, Inc., www.arthrex.com, 2014, 24 pp.
Midfoot Plating Techniques Surgical Technique, Arthrex, Inc., www.arthrex.com, 2014, 14 pp.
Hallux Valgus Solutions, Arthrex, Inc., www.arthrex.com, 2009, 2 pp.
Lisfranc TightRope Fixation Surgical Technique, Arthrex, Inc., www.arthrex.com, 2013, 6 pp.
Low Profile MTP Plate Surgical Technique, Arthrex, Inc., www.arthrex.com, 2012, 4 pp.
Low Profile Plate and Screw System Surgical Technique, Arthrex, Inc., www.arthrex.com, 2012, 6 pp.
Plaple Fixation System Surgical Technique, Arthrex, Inc., www.arthrex.com, 2013, 4 pp.
QuickFix Staple System Surgical Technique, Arthrex, Inc., www.arthrex.com, 2010, 4 pp.
Distal Extremities Orthopedic Update, Arthrex, Inc., www.arthrex.com 2012, 24 pp.
O'Neill, P., et al., "Hallux Valgus Correction: A Comparison of IM Angle and 1st MTC Joint Pressure Before and After Correction", Arthrex, Inc., www.arthrex.com, 2008, 2 pp.
Foot & Ankle Repair and Reconstruction Technology Brochure, Arthrex, Inc., www.athrex.com, 2016, 86 pp.
Comprehensive Solutions for Forefoot and Midfoot Surgery Using the Mini TightRope System, Arthrex, Inc., www.arthrex.com, 2012, 15 pp.
Plantar Lapidus Plate Surgical Technique, Arthrex, Inc., www.arthrex.com, 2015, 6 pp.
A.L.P.S. Total Foot System Sales Sheet, Biomet Trauma, www.biomet.com, 2014, 10 pp.
Clover Staple, BioPro Biologically Oriented Prostheses, Brochure No. 19140, Rev. 1, 2 pp.
Dayton, Paul, et al., "Comparison of the Mechanical Characteristics of a Universal Small Biplane Plating Technique Without Compression Screw and Single Anatomic Plate with Compression Screw", The Journal of Foot & Ankle Surgery, www.jfas.org, 2016, pp. 1-5.
Foot Surgery Innovation in Forefoot Reconstruction, DePuy Orthopaedics, Inc., www.depuy.com, Aug. 2011, 36 pp.
The Flower Akin Plate Procedure Guide, Flower Orthopedics, www.flowerortho.com, Apr. 2015, 8 pp.
Hallux Intramedullary Fusion Device Surgical Technique, Extremity Medical, www.extremitymedical.com, Sep. 2012, 12 pp.
I.B.S. Innovative Bone Synthesis Overview, Athrodax Healthcare International Ltd., www.arhrodax.co.uk, Oct. 2014, 4 pp.
D.L.P. Dorsal Lisfranc Plate, Integra Lifesciences Corporation, www.integra-LS.com, 2007, 20 pp.
The IO Fix Advantage: Designed for Fusion, Extremity Medical, www.extremitymedical.com, 2012, 4 pp.
IO Fix Plus Intraosseous Fixation Surgical Technique, Extremity Medical, www.extremitymedical.com, 2012, 20 pp.
12 mm Memory Staples 20 mm Arthrodesis Memory Staples for Arthrodesis and Phalangeal Osteotomies, DePuy International Ltd., 2004, 4 pp.
Memory Staple Surgical Technique, DePuy Orthopaedics, Inc. 2006, 16 pp.
ALPS Total Foot System Product Rationale & Surgical Technique, DePuy Orthopaedics, Inc., 2011, 136 pp.
Re+Line Bunion Correction System Surgical Technique and Product Guide, Nextremity Solutions, nextremitysolutions.com, 2015, 9 pp.
VLP Foot Variable-Angle Locked Plating System Surgical Technique, Smith & Nephew, www.smith-nephew.com, Mar. 2010, 28 pp.
2.4 mm/2.7 mm Variable Angle LCP Forefoot/Midfoot System—Procedure Specific Plates for Osteotomies, Fusions and Fractures of the Foot, Synthex (USA), www. synthes.com, Mar. 2011, 95 pp.
The Locking Calcaneal Plate. Part of the Synthes Small Fragment Locking Compression Plate (LCP) System. Synthes GmbH, www.depuysynthes.com, 2015, 20 pp.
Variable Angle LCP TMT Fusion Plates 2.4/2.7 Part of the Variable Angle LCP Forefoot/Midfoot System 2.4/2.7, DePuy Synthes, Synthes GmbH, www.depuysynthes.com, 2015, 36 pp.
2.4 mm/2.7 mm Variable Angle LCP Forefoot/Midfoot System. Procedure-Specific Plates for Osteotomies, Fusions and Fracturews of the Foot. Synthes (USA), www.synthes.com, 2010, 95 pp.
Claw II, Polyaxial Compression Plating System with Ortholoc 3DSi Locking Screw Technology Surgical Technique, Wright Medical Technology, Inc., www.wmt.com, 2011, 18 pp.
Charlotte Quick Staple, Wright Medical Technology, Inc., www.wmt.com, 2007, 2 pp.
Darco MFS, Locked Plating System for Reconstructive Forefoot Surgery, Wright Medical Technology, Inc., www.wmt.com, 2010, 8 pp.

* cited by examiner

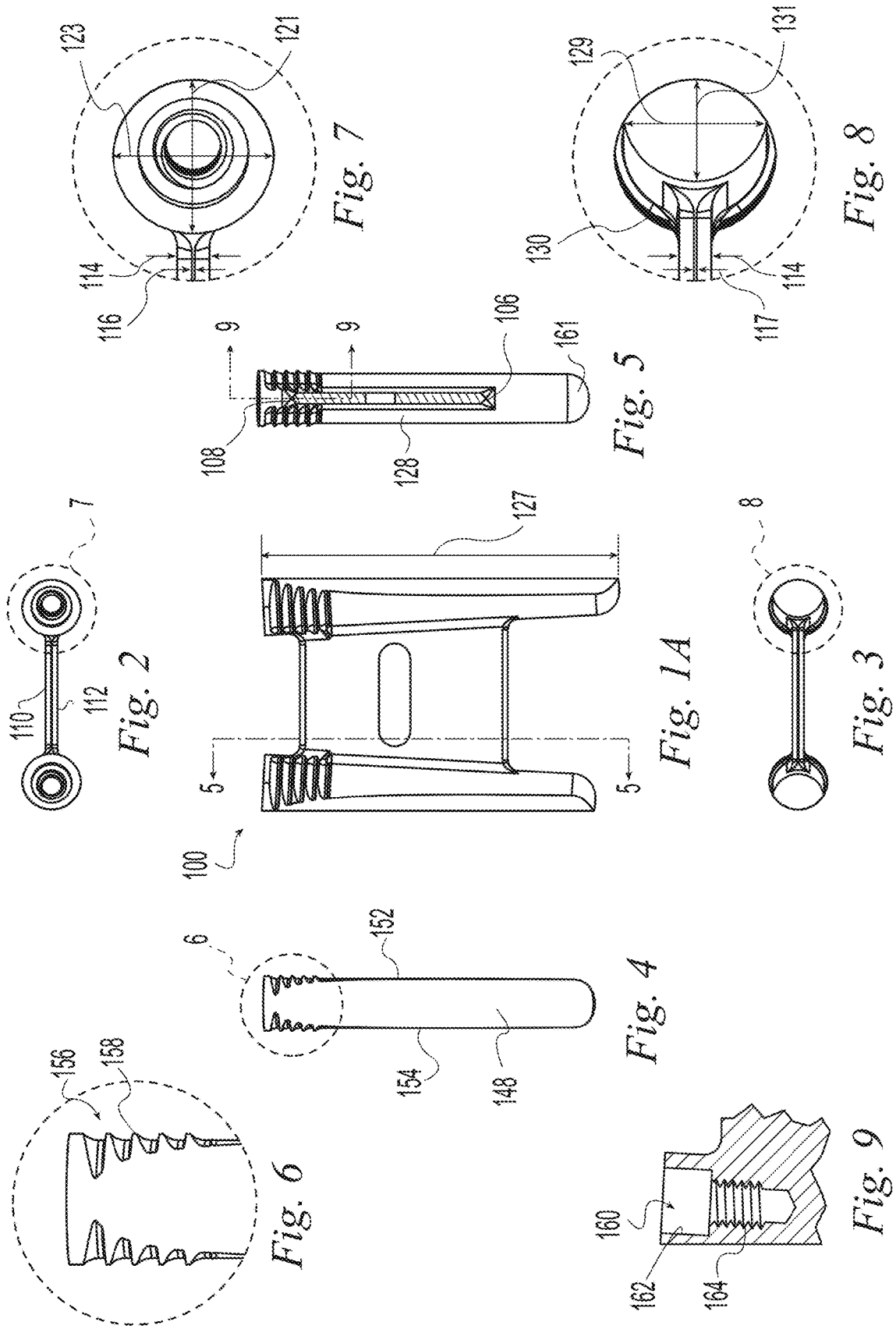

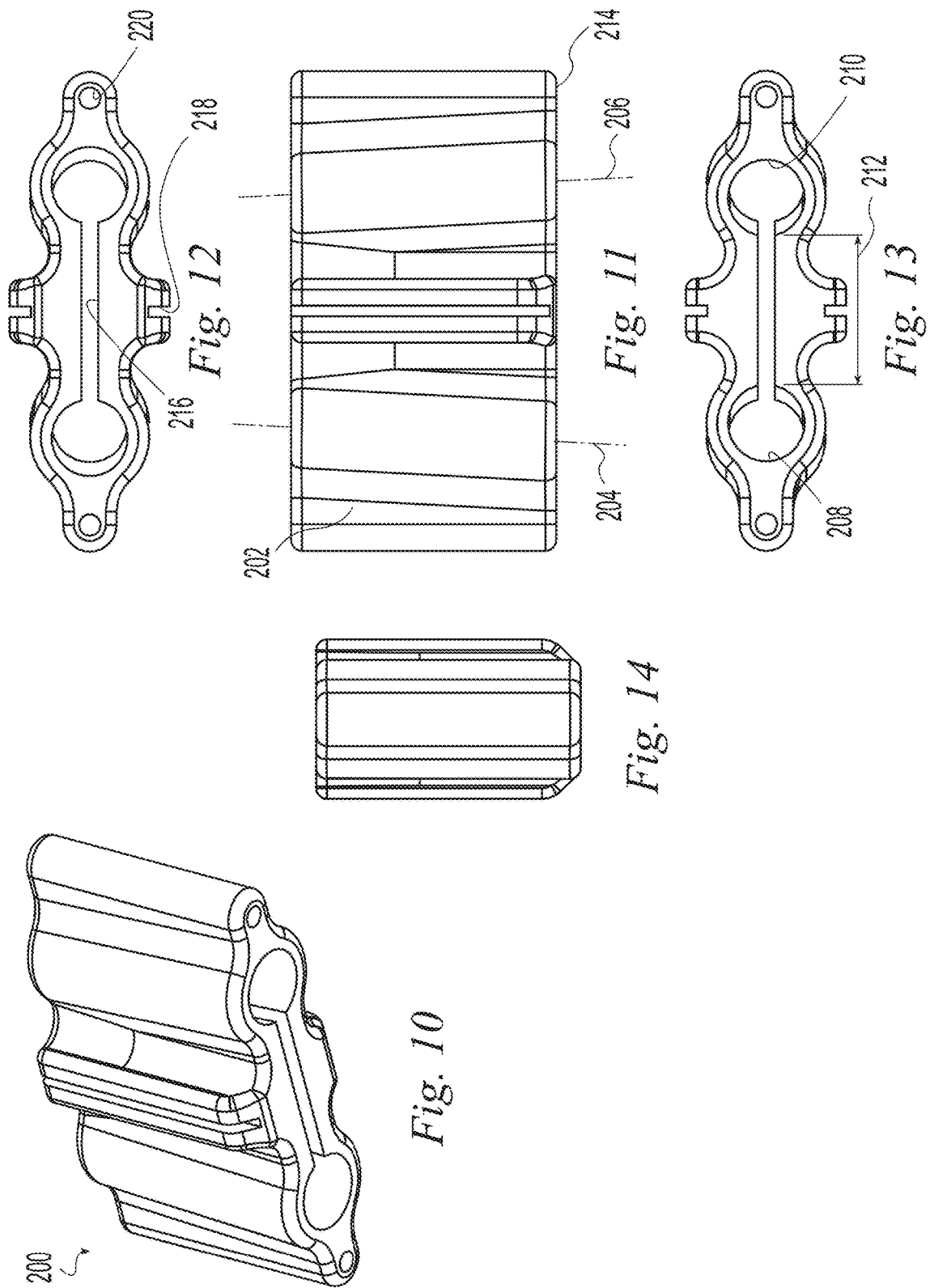

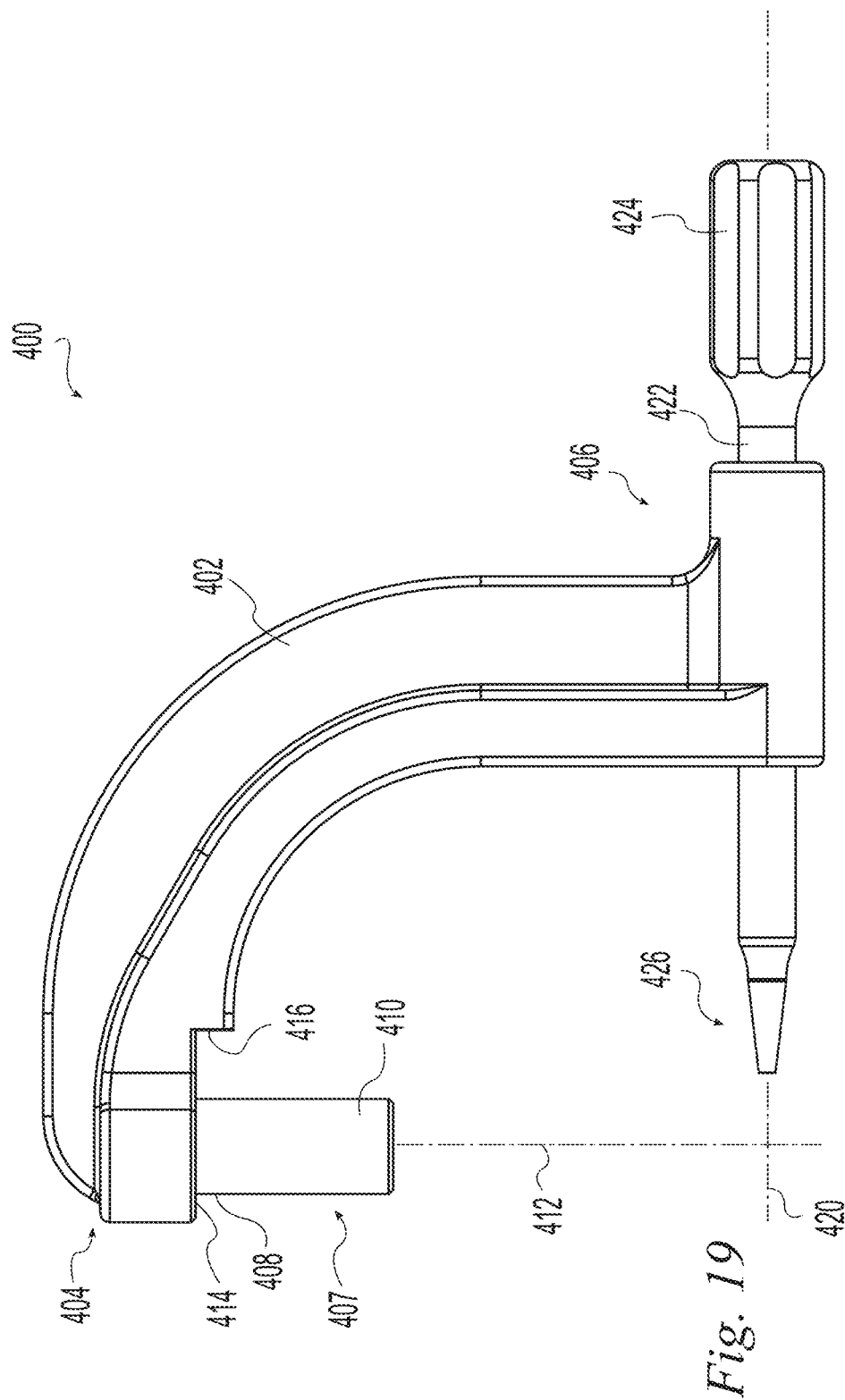

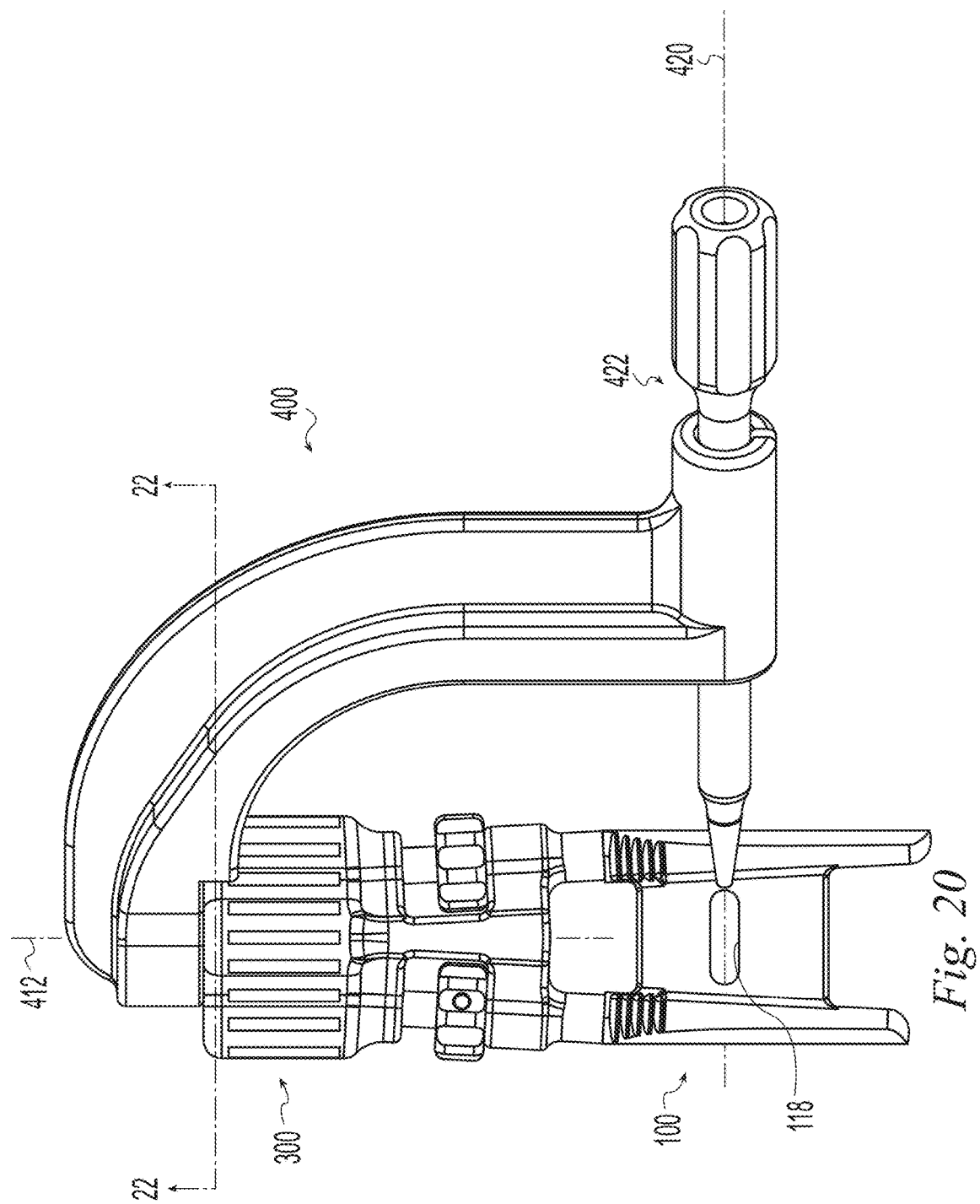

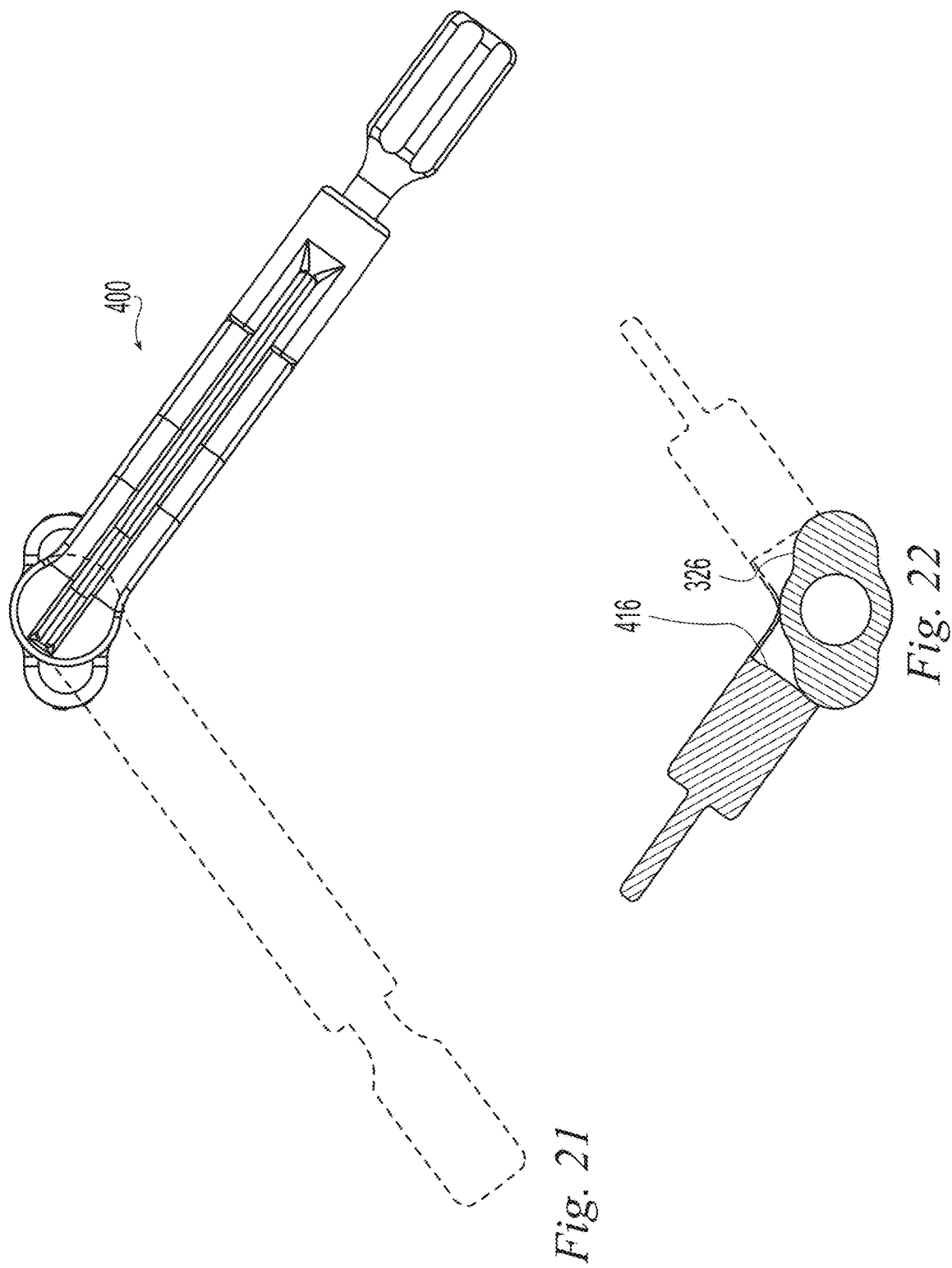

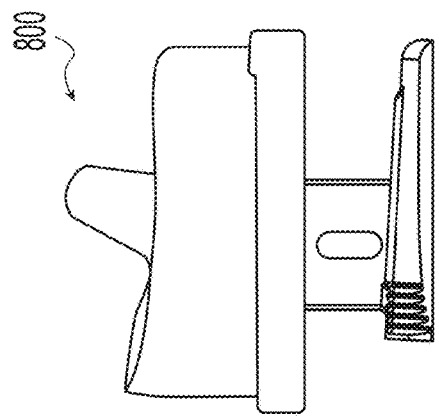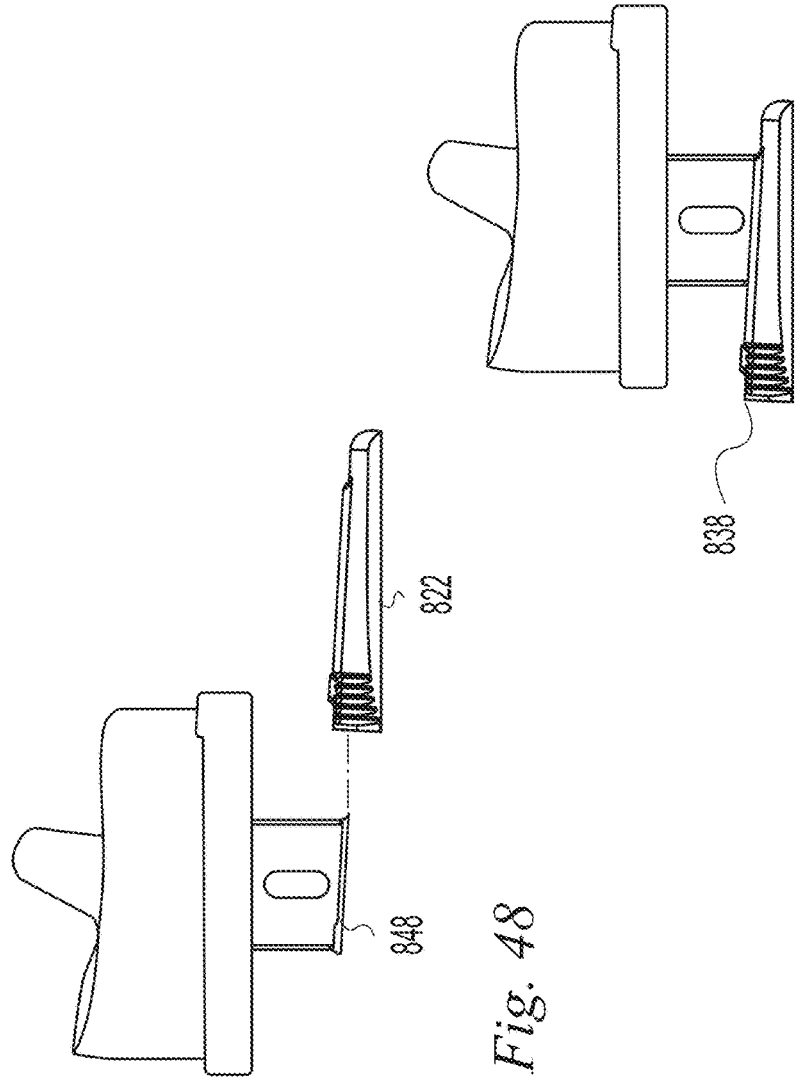

ORTHOPEDIC FASTENERS, INSTRUMENTS AND METHODS

CROSS-REFERENCE TO RELATED APPLICATIONS

This application claims the benefit of U.S. Provisional Application No. 62/188,185, filed Jul. 2, 2015, and U.S. Provisional Application No. 62/308,011, filed Mar. 14, 2016, all of which are hereby incorporated by reference.

FIELD OF THE INVENTION

Examples of the invention relate to methods, implants, and instruments for compressing first and second bone portions or a bone portion and an implant together.

BACKGROUND

Various conditions may affect skeletal joints such as the deterioration, elongation, shortening, or rupture of soft tissues, cartilage, and/or bone associated with the joint and consequent laxity, pain, and/or deformity. It may be desirable to change the angular alignment of a bone or a portion of a bone to restore function and/or reduce pain. It likewise may be desirable to fuse a joint to fix the bones of the joint in a better angular alignment or reduce pain caused by motion at the joint. It may also be desirable to support a fractured bone to allow healing of the fracture to occur. It may also be desirable to support an implant on a bone. To this end, various osteotomy procedures, joint fusion procedures, fracture fixation procedures, joint resurfacing procedures, implants and instruments have been proposed. Such procedures have been performed throughout the body to make various angular adjustments in, fuse joints associated with, fuse fractures associated with, and/or resurface articular surfaces of tibia, fibula, femur, pelvis, humerus, ulna, radius, carpal, metacarpal, tarsal, metatarsal, phalangeal and other bones.

SUMMARY

Examples of the invention provide methods, implants, and instruments capable of compressing first and second bone portions or a bone portion and an implant together. The bone portions may be portions of the same bone as in a fracture or osteotomy. The bone portions may be portions of different bones as in arthrodesis. A bone portion may be a portion of a bone adjacent an articulating joint and the implant may be a resurfacing implant, a spacer, and/or a fusion supporting implant.

BRIEF DESCRIPTION OF THE DRAWINGS

Various examples of the invention will be discussed with reference to the appended drawings. These drawings depict only illustrative examples of the invention and are not to be considered limiting of its scope.

FIG. 1A is front elevation view of a bone implant according to one example of the invention;
FIG. 2 is a top view of the bone implant of FIG. 1;
FIG. 3 bottom view of the bone implant of FIG. 1;
FIG. 4 is a side elevation view of the bone implant of FIG. 1;
FIG. 5 is a cross sectional view of the bone implant of FIG. 1 taken along line 5-5 of FIG. 1A;
FIG. 6 is a detail view of the bone implant of FIG. 1;
FIG. 7 is a detail view of the bone implant of FIG. 1;
FIG. 8 is a detail view of the bone implant of FIG. 1;
FIG. 9 is a detail view of the bone implant of FIG. 1;
FIG. 10 is a perspective view of an example of a hole forming guide for the bone implant of FIG. 1;
FIG. 11 is a front elevation view of the hole forming guide of FIG. 10;
FIG. 12 is a top view of the hole forming guide of FIG. 10;
FIG. 13 is a bottom view of the hole forming guide of FIG. 10;
FIG. 14 is a side elevation view of the hole forming guide of FIG. 10;
FIG. 19 is a front elevation view of an example of a fixation guide for the bone implant of FIG. 1;
FIG. 20 is a perspective view of the fixation guide of FIG. 19 with the inserter of FIG. 15 and the implant of FIG. 1;
FIG. 21 is a top view of the fixation guide of FIG. 19 with the inserter of FIG. 15 and the implant of FIG. 1 illustrating range of motion;
FIG. 22 is a cross sectional view taken along line 22-22 of FIG. 20 and illustrating range of motion;
FIGS. 48-50 are side elevation views of the implant of FIG. 45 illustrating the motion of component 822.

DESCRIPTION OF THE ILLUSTRATIVE EXAMPLES

Figure 1B:
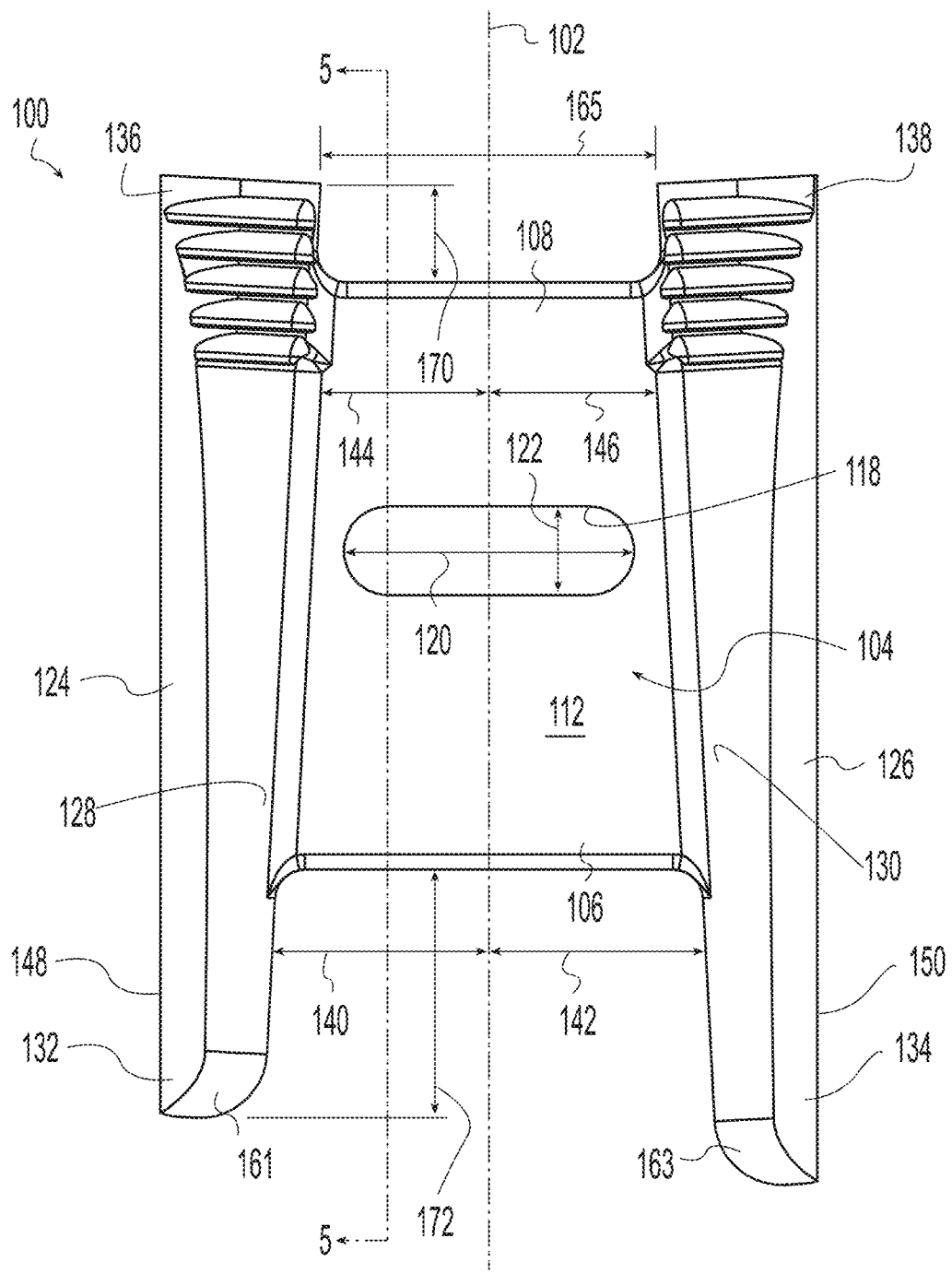
FIG. 1B is an enlarged front elevation view of the bone implant of FIG. 1.

The following illustrative examples describe methods, implants, and instruments capable of compressing first and second bone portions or a bone portion and an implant together. The bone portions may be portions of the same bone that have become separated due to a fracture or an osteotomy. The bone portions may be portions of different bones as in an arthrodesis performed to fuse a joint. A bone portion may be a portion of a bone adjacent an articulating joint and the implant may be a resurfacing implant, a spacer, and/or a fusion supporting implant. Examples of the invention may be used with any bone or joint including but not limited to bones such as a tibia, fibula, femur, pelvis, humerus, ulna, radius, carpal, metacarpal, tarsal, metatarsal, phalange and joints associated therewith.

The term "transverse" is used herein to mean crossing as in non-parallel.

Examples according to the invention provide methods, implants, and instruments capable of compressing first and second bone portions or a bone portion and an implant together. FIGS. 1-9 illustrate an example in the form of a fastener 100 for joining first and second bone portions. The fastener includes an insertion axis 102 along which the fastener moves as it is inserted into or removed from a bone. The fastener 100 has a body 104 extending between a body distal or leading end 106 and a body proximal or trailing end 108. The body leading end 106 and the body trailing end 108 are spaced from one another longitudinally relative to the insertion axis. In the illustrative example of FIGS. 1-9, the body 104 has a generally planar configuration with opposed planar sides 110, 112 spaced apart a body thickness 114. The opposed planar sides 110, 112 converge toward the body trailing end 108 to define a trailing edge having a trailing edge thickness 116 that is less than the body thickness 114 (FIG. 7). The relatively narrow trailing edge thickness 116 facilitates removal of the fastener 100 after bone has healed over the body trailing end 108. During removal, such as in a revision procedure, the narrow trailing edge will cut through overlying bone. In the illustrative example of FIGS. 1-9, the opposed planar sides 110, 112 also converge toward the body leading end 106 to define a leading edge having a leading edge thickness 117 that is less than the body thickness 114. The relatively narrow leading edge thickness 117 facilitates insertion of the fastener 100.

In the illustrative example of FIGS. 1-9, the body 104 has an aperture 118 extending through the body 104 between the opposed planar sides 110, 112. The aperture 118 has a length 120 and a width 122. In the illustrative example of FIGS. 1-9, the aperture length 120 is greater than the aperture width 122 and the aperture length 120 is oriented transverse to the insertion axis 102. In the illustrative example of FIGS. 1-9, the aperture length is oriented normal to the insertion axis. The inclusion of an aperture and its size and orientation are determined for the particular application in which the fastener is to be used. For example, the aperture may receive a fixation member, such as screw 636 in FIG. 36, to provide cross fixation of the bone portions and to prevent the fastener 100 from migrating out of the bone.

The fastener 100 includes first and second legs 124, 126 connected to the body. The legs have a width 121, a depth 123 (FIG. 7), and a length 127 (FIG. 1A). The first and second legs may be the same size or they may be different sizes to accommodate particular anatomy. For example, the legs may have the same width and depth but have different lengths so that they can accommodate bi-cortical fixation in bone portions of varying thickness. Each leg has an elongate inboard surface 128, 130 facing the insertion axis 102 and extending from a leading end 132, 134 to a trailing end 136, 138. The elongate inboard surface 128, 130 is spaced from the insertion axis 102 a leading distance 140, 142 near the leading end and the elongate inboard surface is spaced from the insertion axis 102 a trailing distance 144, 146 near the trailing end. The leading distance 140, 142 and trailing distance 144, 146 for each leg may be equal such that the inboard surface is parallel to the insertion axis 102. The leading distance 140, 142 and trailing distance 144, 146 for each leg may be unequal such that, for example, one or both of the leg inboard surfaces may converge or diverge distally from the insertion axis 102. Preferably, at least one of the leading distances 140, 142 is greater than the corresponding trailing distance 144, 146 and the other leading distance 140, 142 is equal to or greater than the corresponding trailing distance 144, 146 such that the inboard surfaces 128, 130 diverge relative to one another distally or in other words in the leading direction defined by the leading ends and at least one diverges from the insertion axis 102. In the illustrative example of FIGS. 1-9, each leg diverges from the insertion axis 102 in the leading direction. Preferably the inboard surfaces 128, 130 each diverges from the insertion axis 102 by a divergence angle. The included angle between the inboard surfaces 128, 130 is the sum of the individual divergence angles. As described above, the may diverge symmetrically or asymmetrically. The individual divergence angles are preferably in the range of 1-5 degrees. In the illustrative example of FIGS. 1-9, the divergence angles are each 3 degrees yielding an included angle of 6 degrees. When the legs are positioned in bone, the projected area of each leg perpendicular to the insertion axis affects the resistance of the leg to pulling through the bone. The larger the projected area the greater the pull through strength. For a given leg length, the area is determined by the leg depth, or for a cylindrical leg by its diameter. The body is inserted into a slot formed in the bone between the legs. As the slot width increases relative to the leg projected area, the resistance of the leg to being pulled into the slot decreases. Thus, a thinner body and consequently thinner slot increases pull through strength. This can be expressed in terms of the difference between the leg depth and body thickness or in terms of a ratio of leg depth to body thickness.

In the illustrative example of FIGS. 1-9, each leg 124, 126 further includes an elongate outboard surface 148, 150 facing away from the insertion axis 102 and extending from the leading end to the trailing end. In the illustrative example of FIGS. 1-9, the elongate outboard surfaces 148, 150 are parallel to one another and the insertion axis 102.

In the illustrative example of FIGS. 1-9, the fastener legs 124, 126 have a generally elliptical cross section. Near the trailing end the cross section is approximately circular. Near the distal end, the legs are non-circular having a major diameter 129 greater than a minor diameter 131 (FIG. 8). In the illustrative example of FIGS. 1-9, the leg shape can be describes as being a pair of cylinders that diverge toward the leading end with material removed on the outboard surfaces so that the outboard surfaces are rendered parallel. The resulting legs are circular at the trailing end as seen in FIG. 7 and transition into the shape of intersecting circles as the material is removed, becoming narrower, i.e. tapering, in the minor axis toward the leading end as seen in FIG. 8. The front 152 and back 154 of each leg are parallel as seen in FIG. 4. The trailing end of each leg includes barbs 156 as seen in FIG. 6. The barbs 156 are generally in the form of upwardly swept circular projections 158 on the front, back and inboard surfaces of the trailing portion of the leg such as would result if the barbs were circular projections surrounding divergent cylindrical legs and material was removed on the outboard surfaces so that the outboard surfaces were rendered parallel and consequently removing progressively more of the circular projections in the leading direction. Alternatively, the barbs may extend completely around the circumference of the leg. The trailing ends of the legs include a cavity 160 (FIG. 9) operable to couple with an inserter as described below. Preferably the cavity is threaded to receive a threaded connector. In the illustrative example of FIGS. 1-9, the cavity 160 is a stepped cylindrical cavity with a larger diameter trailing portion 162 and a smaller diameter, threaded leading portion 164. The leading end of each leg includes a radius 161, 163 to ease insertion of the fastener 100 into holes formed in bone. The inboard surfaces 128, 130 of the legs have an inboard surface trailing end spacing 165 at the trailing end of the legs. The trailing end of the body 108 is recessed toward the leading end of the legs by a trailing end recess distance 170. The leading end of the body 106 is recessed toward the trailing end of the legs by a leading end recess distance 172. The recess distances 170, 172 are preferably equal to or greater than a bone cortex thickness at a location at which the fastener is to be used so that the body 104 is located inward of the cortical bone when the fastener is installed.

The various sizes and proportions for the fastener will vary based on the application. For example, depending on the application, leg depth preferably ranges from 2 mm to 7 mm and the body thickness preferably ranges from 0.5-5 mm. Further for example, in many applications, such as for use in the mid and fore regions of the hands and feet, a fastener may advantageously have a leg depth of 2.5-4.5 mm and a body thickness of 0.5-1.5 mm. The ratio of leg depth to body thickness preferably ranges from 14:1 to 1.5:1. More preferably, the ratio ranges from 5:1 to 3:1.

In the illustrative example of FIGS. 1-9, the leg width is constant and equal to the leg depth at the proximal end of the leg.

As stated above, the body leading and trailing end recess distances 170, 172 are preferably equal to or greater than the local bone cortex thickness. The distances 170, 172 are preferably be in the range of 1-8 mm and may vary for different size staples and different applications.

The leg length 127 is preferably close to the bone thickness along the insertion axis 102. The legs may be the same length or different lengths and they may be staggered at one or both ends. In the illustrative example of FIGS. 1-9, the leg lengths are different and the legs are level at the proximal end but staggered at the distal end. For use in foot surgery, the leg lengths are preferably in the range of 10-50 mm and more preferably in the range of 14-32 mm. For use at other locations, the leg length may be outside of these ranges and can be, for example, quite long in large staples for applications such as tibial osteotomies.

The aperture 118, if present, is sized to receive an appropriate cross fixation fastener. Preferably its length 120 is as long as possible, and corresponds to an angular variation, that gives maximum flexibility for cross fixation placement without colliding with the legs.

The fastener 100 may be provided as a plurality of fasteners having different sizes to accommodate different anatomy. In one example, the fastener is provided as a plurality of fasteners of varying leg length 127 with the leg width 121, depth 123, outboard wall 148, 150 spacing, and divergence angle being the same for each fastener. In this way differing bone thicknesses may be accommodated while using the same instruments described below.

Referring to FIGS. 10-14, a hole forming guide 200 includes a body 202 defining hole axes 204, 206 along which a hole forming tool may be guided. In the illustrative example of FIGS. 10-14, the axes 204, 206 are defined by cylindrical guide holes 208, 210. The guide holes 208, 210 are operable to receive a hole forming tool such as a punch or drill and constrain the hole forming tool to longitudinal motion along the axes 204, 206 to form holes in an underlying bone. The axes 204, 206 are angled to correspond to the divergent legs of the fastener of FIGS. 1-9. The inboard surfaces of the guide holes 208, 210 have a guide hole inboard surface leading end spacing 212 at the leading end 214 of the guide 200 that is equal to or greater than the inboard surface trailing end spacing 165 of the fastener. If the guide hole inboard surface leading end spacing 212 is equal to the fastener leg inboard surface trailing end spacing 165, the inboard surfaces 128, 130 of the fastener legs will just touch the inboard surfaces of the bone holes when the fastener leg trailing ends are inserted flush with the bone surface. Further seating of the fastener legs below the surface of the bone will result in compression of the bone between the fastener legs. Likewise, if the guide hole inboard surface leading end spacing 212 is greater than the fastener leg inboard surface trailing end spacing 165, the inboard surfaces 128, 130 of the fastener legs will just touch the inboard surfaces of the bone holes when the fastener leg trailing ends are proud of the bone surface. Further insertion of the fastener until the trailing ends of the legs are flush with the bone surface will result in compression of the bone. The amount of compression for a given insertion depth of the fastener may be determined by selecting the relationship of guide hole inboard surface leading end spacing 212 to fastener leg inboard surface trailing end spacing 165. With the included angle between the leg inboard surfaces matching the included angle between the hole inboard surfaces, the compression of the bone between the fastener legs is uniform at all positions between the legs normal to the insertion axis and inserting the bone fastener does not create a relative bending moment between the first and second bone portions. The guide 200 further includes a guide slot 216 connecting the holes 208, 210. The slot 216 may be used to guide a chisel, broach, saw or other cutting tool to remove bone and form a connecting slot between bone holes formed using the guide holes 208, 210 for receiving the fastener body 104. Alignment notches 218 are provided to indicate the center of the guide 200. Fixation holes 220 are provided to receive fixation pins or screws to fix the guide in position on a bone.

Referring to FIGS. 15-18, an inserter 300 is configured for use with the fastener 100 of FIGS. 1-9. The inserter 300 includes a body 302 having a distal end 304 and a proximal end 306 including a handle portion 308. The body includes a pair of laterally spaced passages extending from the distal end 304 toward the proximal end 306 and each defining a passage axis 307. The passage axes 307 are angled 309 to align with the cavities 160 in the fastener 100. Side cuts or windows 310 communicate with the passages. Each passage receives a locking bolt 312 in axial sliding and rotating relationship. Each bolt 312 traverses one of the windows 310 exposing the portion of the bolt 312 within the window for manipulation. A knob 314 is fixed to each bolt 312, such as by pinning, to allow a user to rotate the bolt 312 about the passage axis 307 and to serve as a limit to axial travel of the bolt 312 as the knob abuts the proximal or distal margins 316, 318 of the window 310. Each bolt 312 includes a smooth cylindrical portion 320 sized to fit into the trailing portion 162 of the stepped cylindrical cavity 160 in one of the fastener legs. Each bolt 312 includes a threaded portion 322, distal to the smooth portion 320, sized to screw into the threaded leading portion 164 of the stepped cavity 160. The proximal end 306 of the inserter 300 includes an engagement portion configured to rotationally couple to a cross fixation guide discussed further below. In the illustrative example of FIGS. 15-18, the engagement portion includes a socket 324 extending distally into a top surface 325 of the handle portion 308 and a peripheral edge 326.

Figure 18:
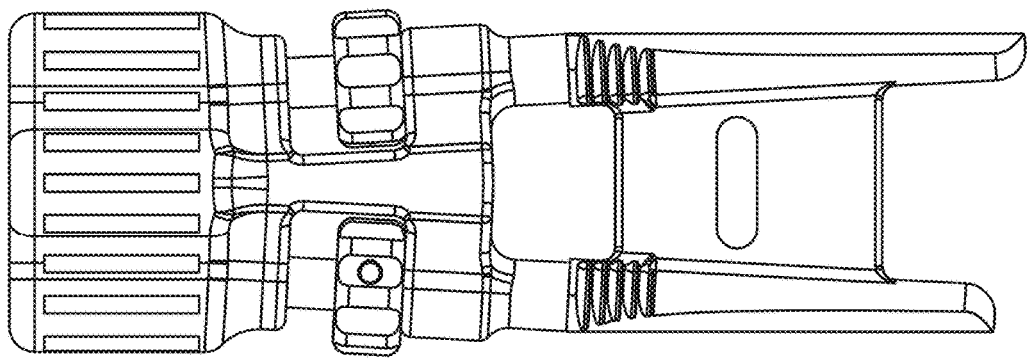
FIGS. 17 and 18 are front elevation views of the inserter of FIG. 15 with the implant of FIG. 1.
Figure 17:
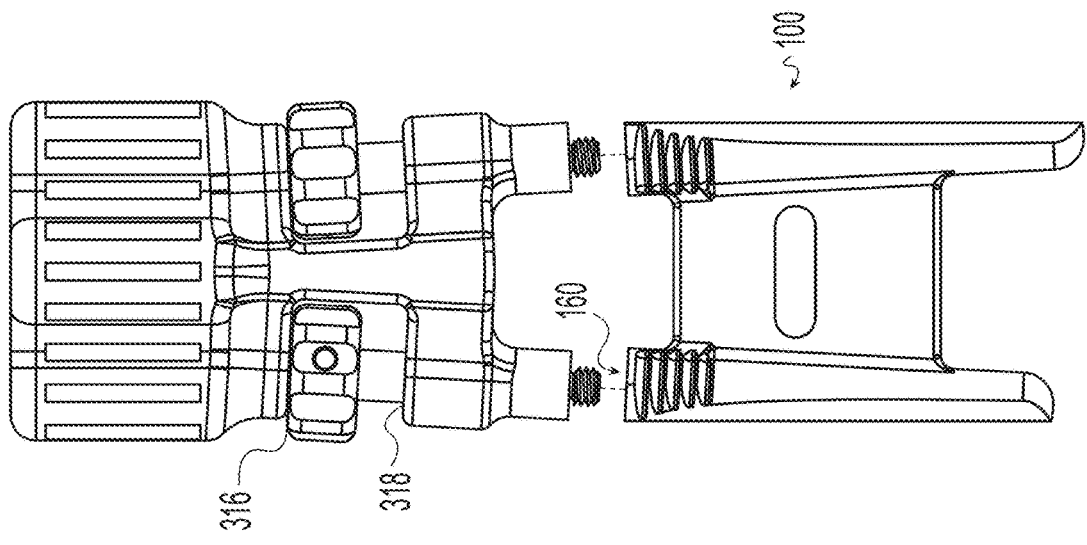
Figure 16:
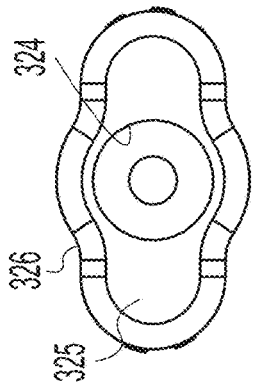
FIG. 16 is a top view of the inserter of FIG. 15.
Figure 15:
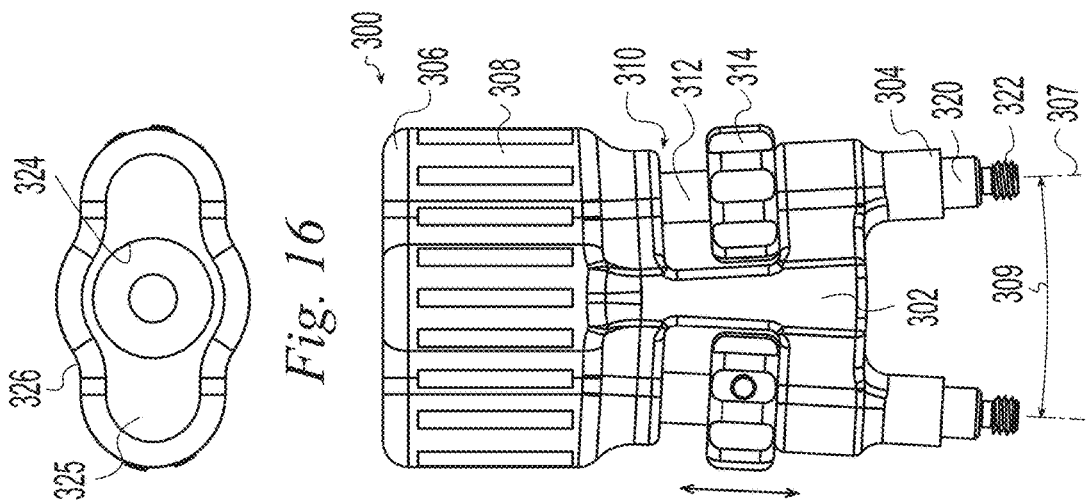
FIG. 15 is a front elevation view of an example of an inserter for the bone implant of FIG. 1.

The inserter 300 is joined to the fastener 100 by first sliding the locking bolts 312 proximally until the knobs 314 abut the proximal margin 316 of the window 310 as shown in FIG. 17. The threaded portion 322 may then be inserted into the cavity 160 of the fastener 100. Each knob 314 is then rotated to thread the locking bolt 312 into the cavity 160 and secure the fastener 100 to the inserter 300 as shown in FIG. 18.

Referring to FIGS. 19-22, a cross fixation guide 400 is engageable with the inserter to guide placement of an elongate member through the aperture 118 of the fastener 100. The elongate member may be a pin, screw, drill, wire or other member. For example, the guide 400 may be used to place a guide wire through the aperture and the guide wire may be used to insert a cannulated screw. The cross fixation guide 400 includes an arcuate guide body 402 having at one end an engagement portion 404 and at an opposite end a guide portion 406. The engagement portion 404 is configured to rotationally couple to the inserter 300. In the illustrative example of FIGS. 19-22, the engagement portion 404 includes a stud 407 extending distally from the guide body 402 from a proximal end 408 to a distal end 410 and defining an engagement axis 412. The guide 400 includes an axial stop and a rotational stop to aid in positioning the guide 400 relative to the inserter 300. In the illustrative example of FIGS. 19-22, a shoulder 414 formed near the proximal end 408 of the stud 407 serves as the axial stop and a side surface 416 transverse to the shoulder 414 and formed on the guide body 402 serves as the rotational stop. The guide portion 406 defines a cross fixation insertion axis 420 transverse to the engagement axis 412 and along which a fixation member may be guided to pass through the fastener aperture 118. In the illustrative example of FIGS. 19-22, the guide portion includes a passage through the guide body 402 defining the cross fixation insertion axis 420 and a sleeve 422 received in the passage in axial sliding relationship. The sleeve 422 includes an axial through passage, proximal handle portion 424 and a distal leading end 426 forming a tapered tip. The axial through passage is sized to guide a guide wire along the cross fixation insertion axis 420. The sleeve may be translated along the axis 420 relative to the guide body 402 to position the leading end 426 at a desired spacing from a bone. The cross fixation guide 400 is coupled to the inserter 300 by inserting the stud 407 into the socket 324 until the shoulder 414 abuts the top surface 325 of the inserter handle 308 as shown in FIG. 20. Thus assembled, the cross fixation insertion axis 420 is aligned with the center of the fastener aperture 118. The cross fixation guide 400 may be rotated relative to the inserter 300 about the engagement axis 412 through an infinite number of angular positions between a first angular position shown in solid line in FIGS. 21 and 22 and a second angular position shown in dashed lines. Preferably, the guide and inserter define stops between them limiting the angular positions. For example, a fixation member to be inserted through the fastener aperture 118, such as screw 636 in FIG. 36, has a longitudinal axis and a transverse dimension normal to the longitudinal axis. The fixation member may be inserted through the aperture 118 at an included angle between the longitudinal axis of the fixation member and the aperture length axis ranging from 90 degrees to a value corresponding to a projected length of the aperture along the fixation member longitudinal axis equal to or greater than the fixation member transverse dimension. Preferably, the angular stops limit the rotation of the guide to be within this range so it is guaranteed that the fixation member will fit through the aperture. In the illustrative example of FIGS. 19-22 the first and second angular positions are limited by abutment of the side surface 416 of the cross fixation guide with the peripheral edge 326 of the inserter 300.

Figure 25:
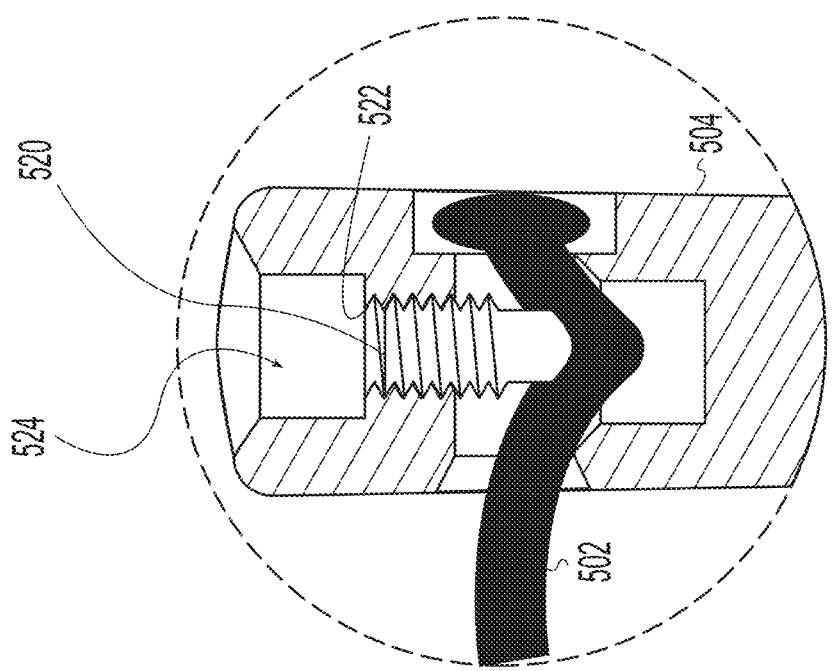
FIG. 25 is a detail view of the bone implant of FIG. 25.
Figure 24:
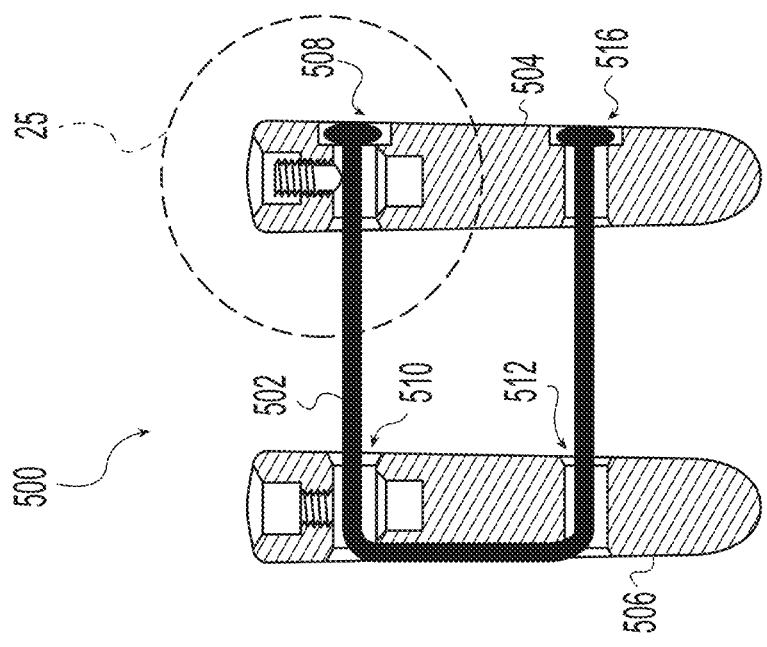
FIG. 24 is a front elevation view of the bone implant of FIG. 23.
Figure 23:
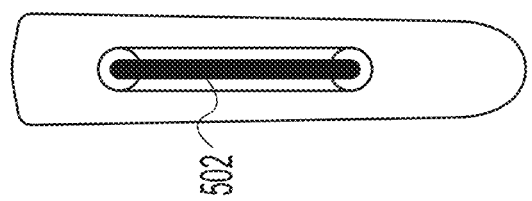
FIG. 23 is a side elevation view of an alternative example of the bone implant of FIG. 1.

FIGS. 23-25 depict another illustrative example of a fastener 500 according to one example of the invention in which the rigid body 104 of fastener 100 has been replaced with a flexible member 502. The fastener includes first and second legs 504, 506. The flexible member 502 connects to axially spaced first and second connectors on the first leg 504 and passes through a receiver on the second leg 506 in sliding relationship to permit the angle between the fastener legs to be varied between arbitrary angles and to facilitate equal tensioning of the flexible member 502. In the illustrative example of FIGS. 23-25, the flexible member 502 is attached at a first location 508 on the first leg 504, extends to the second leg 506, passes through a first passage 510 in the second leg, extends axially along a portion of the second leg, passes through a second passage 512 in the second leg, and returns to the first leg 504 where it is attached at a second location 516. The flexible member 502 is able to slide freely within the passages 510, 512 in the second leg to allow the fastener legs 504, 506 to be variably angled relative to one another and so that tension in the flexible member is distributed equally throughout the flexible member 502. The fastener 500 may include a tensioning device operable to shorten the portion of the flexible member 502 that extends outwardly from the first leg 504. In the illustrative example of FIGS. 23-25, the first leg 504 includes a tensioning member operable to shorten the flexible member, such as for example by pressing the flexible member into the socket 524. For example, a tensioning screw 520 may be engaged with the threaded portion 522 of the socket 524. The flexible member 502 is attached to the first leg 504 so that it passes through the threaded portion 522 distal to the tensioning screw 520. Advancing the tensioning screw 520 presses the flexible member distally into the socket causing a portion of the flexible member 502 to be pulled into the first leg 504 and thus shortening the portion of the flexible member 502 that extends outwardly from the first leg 504. In use, for example, holes may be formed in the bone using a hole guide as in the preceding examples. The legs 504, 506 may be attached to a driver, for example like that of FIG. 15, and inserted into the bone holes. Tensioning screw 520 may then be inserted and advanced to shorten the flexible member and compress the bone.

Figure 26:
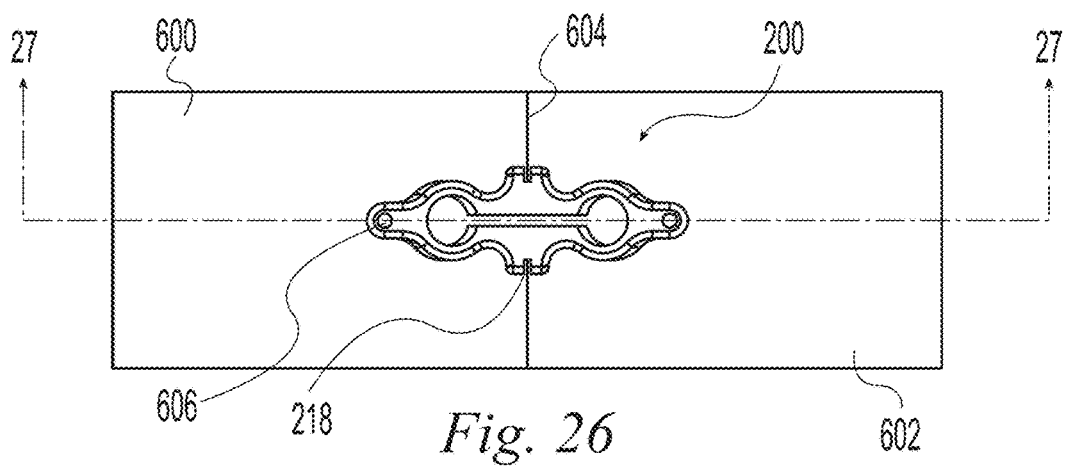
FIGS. 26-37 illustrate an example of a surgical method utilizing the implant of FIG. 1.

FIGS. 26-37 illustrate a method of using the fastener and instruments of FIGS. 1-22. Referring to FIG. 26, first and second bone portions 600, 602 abut at an interface 604 such as a joint articular surface, fracture, osteotomy cut plane, or other interface. The hole forming guide 200 is positioned over the bone portions with the alignment notches 218 aligned with the interface 604 to center the guide 200 over the interface 604. Fixation pins 606 may be placed in holes 220 in the guide 200 to secure the guide 200 to the bone portions.

Figure 27:
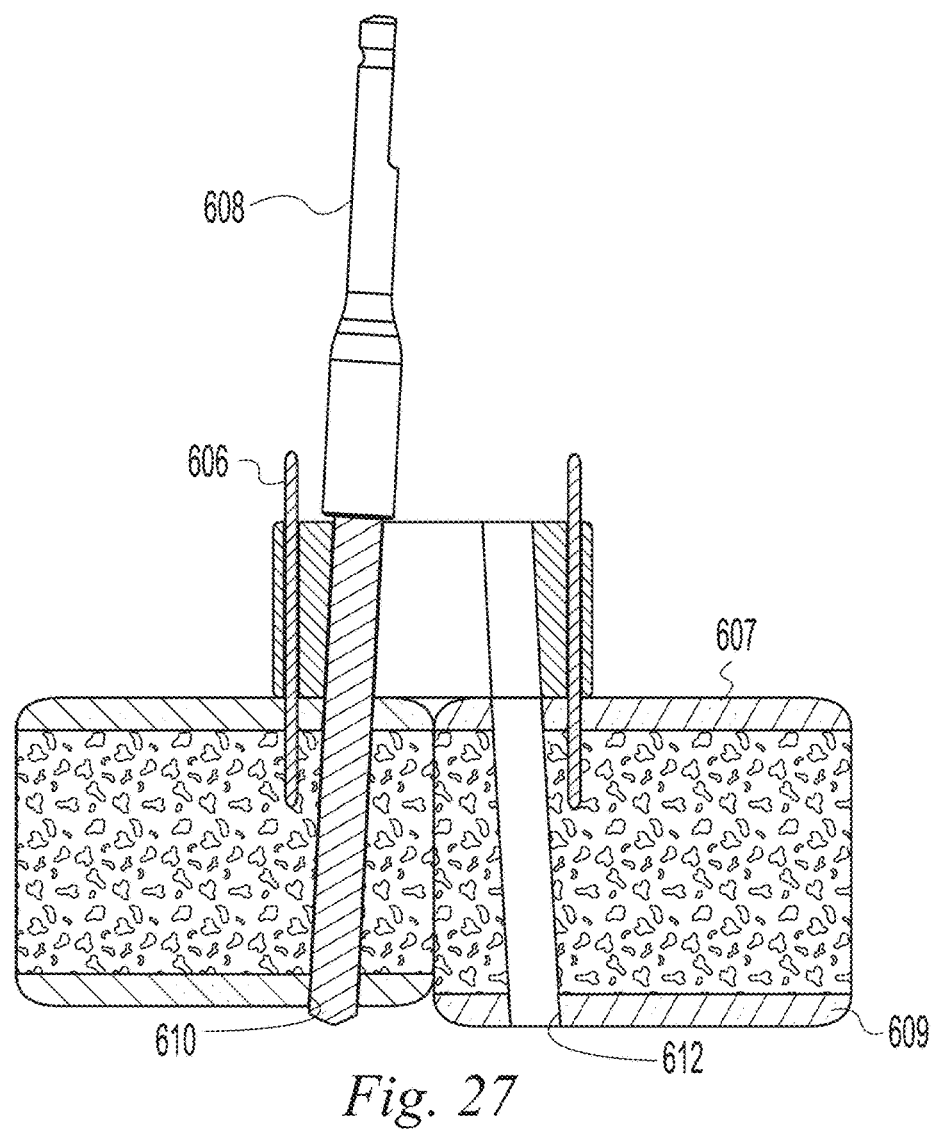

Referring to FIG. 27, a drill 608 is guided in the guide holes 208, 210 to form corresponding holes 610, 612 in the bone. Preferably these holes pass through the bones so that the legs of the fastener 100 will engage the bone portions bi-cortically at the proximal and distal cortices 607, 609.

Figure 28:
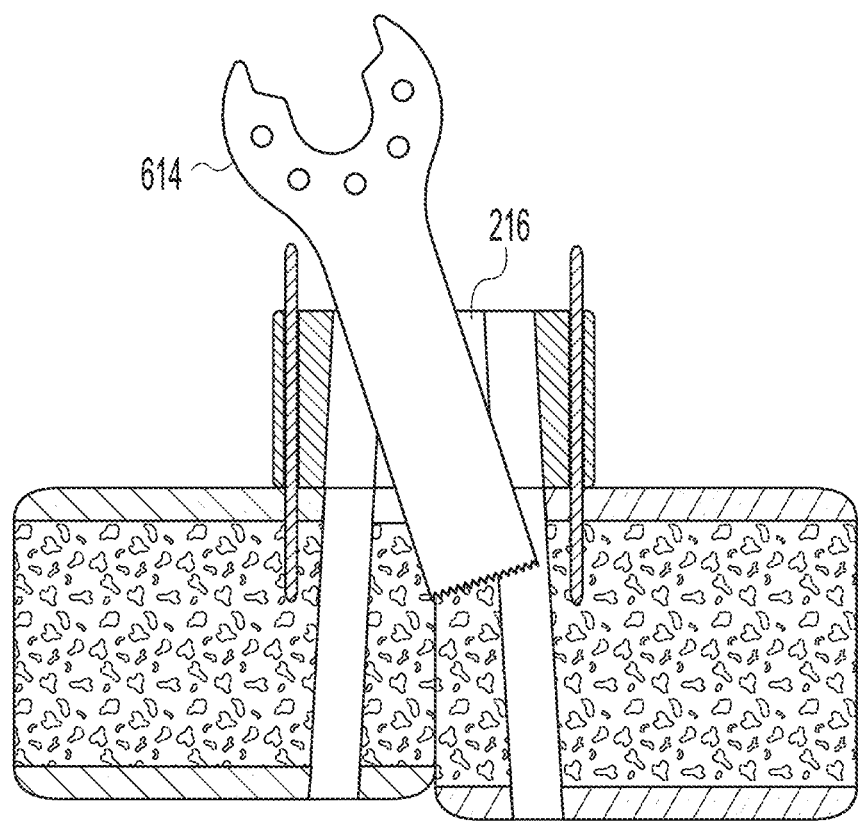
Figure 29:
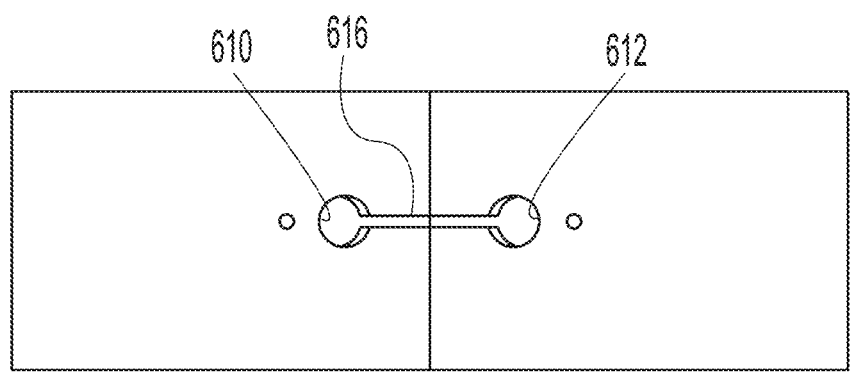

Referring to FIGS. 28 and 29, a saw blade 614 is guided in the saw slot 216 of the guide 200 to form a bone slot 616 to ease insertion of the fastener body through the proximal cortex. Preferably the saw slot only extends through the proximal bone cortex since only a proximal slot is needed to insert the fastener body.

Figure 30:
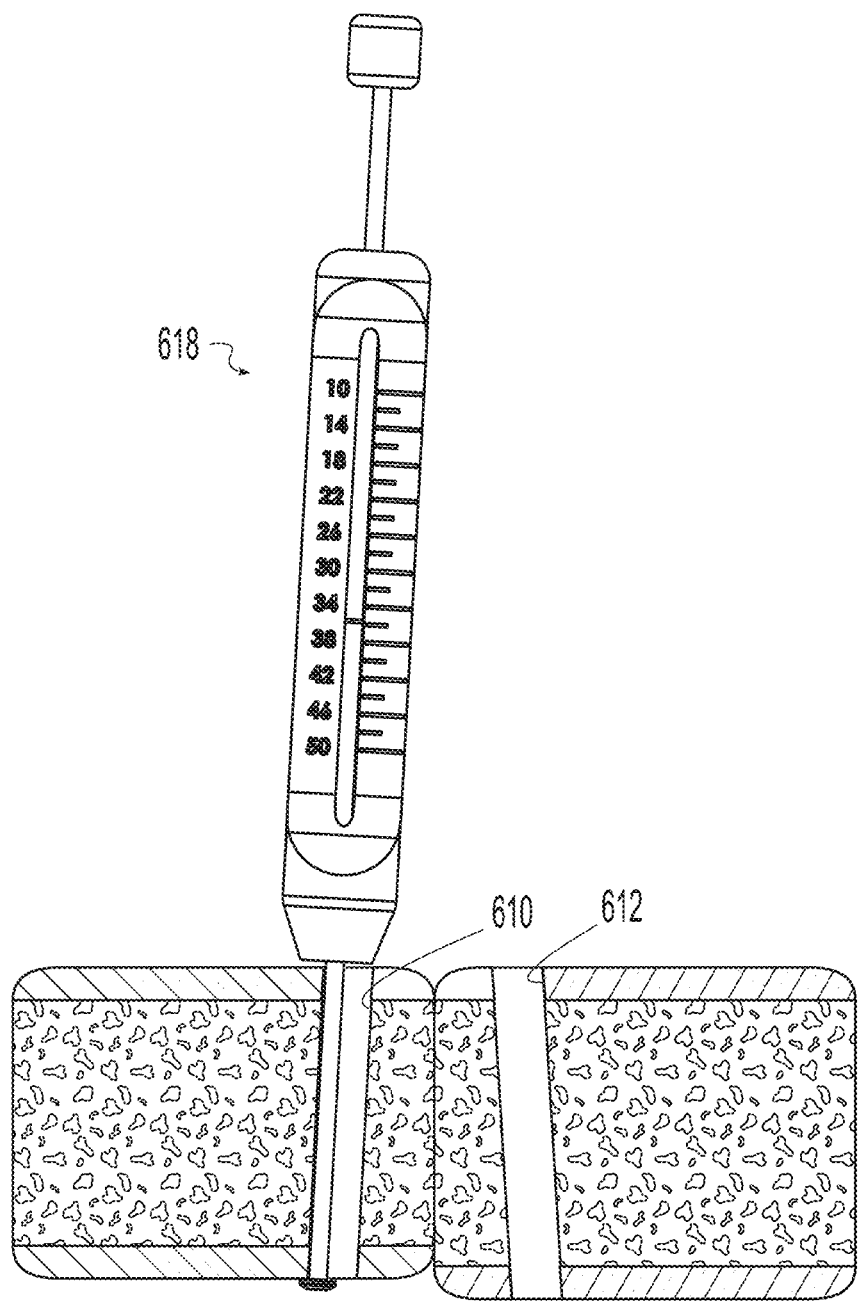

Referring to FIG. 30, a depth gauge 618 is used to probe the bone holes 610, 612 to determine their depth as an aid in selecting a fastener of the appropriate size to provide bi-cortical fixation. Depending on the shape of the bone portions, the holes may have different depths and may preferably receive a fastener having different length legs.

Figure 31:
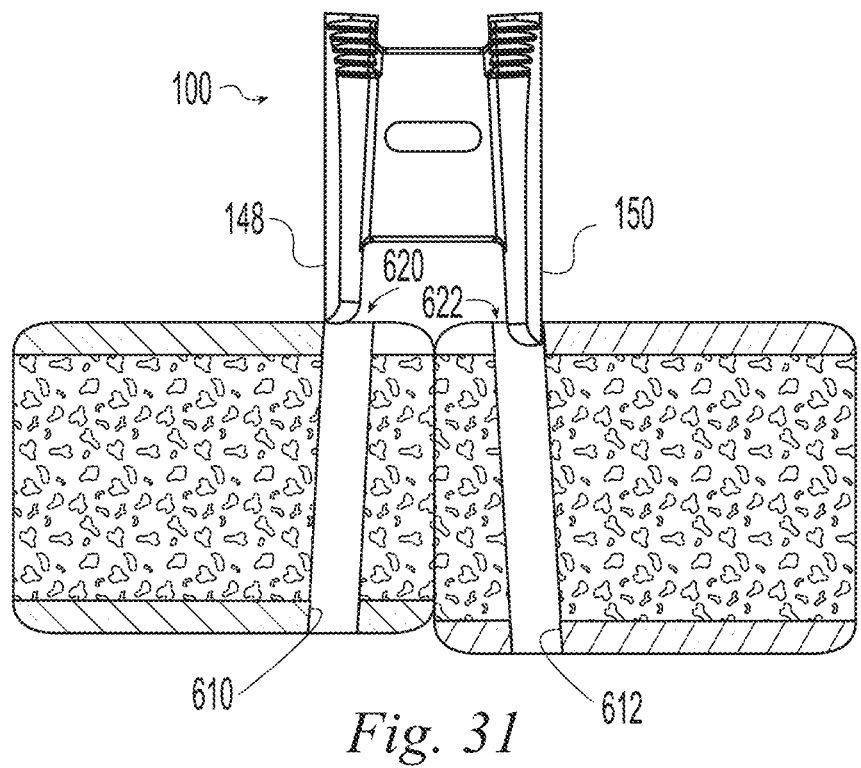
Figure 32:
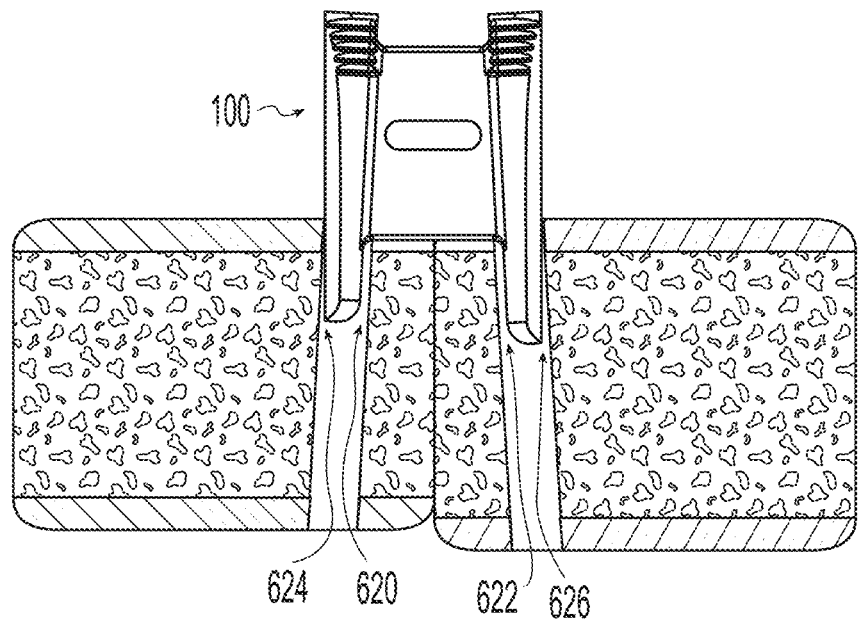

Referring to FIGS. 31 and 32, a fastener 100 is started into the bone holes 610, 612. The inserter 300 has been omitted from the figures to simplify the drawings. The outboard surfaces 148, 150 of the fastener legs are sized to match the proximal spacing of the outboard bone hole walls. Since outboard surfaces 148, 150 are parallel, they stay in contact with the proximal portion of the bone holes 610, 612 as the fastener is advanced into the bone portions. Inboard gaps 620, 622 are present between the fastener legs and the bone holes. Outboard gaps 624, 626 occur between the fastener legs and the bone holes distal of the proximal edge of the bone holes as the fastener is advanced.

Figure 33:
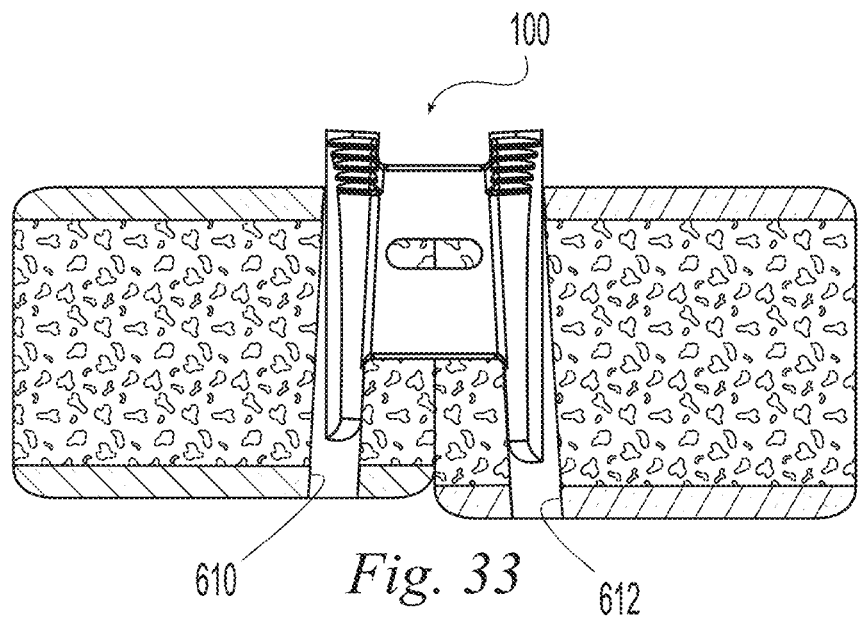
Figure 34:
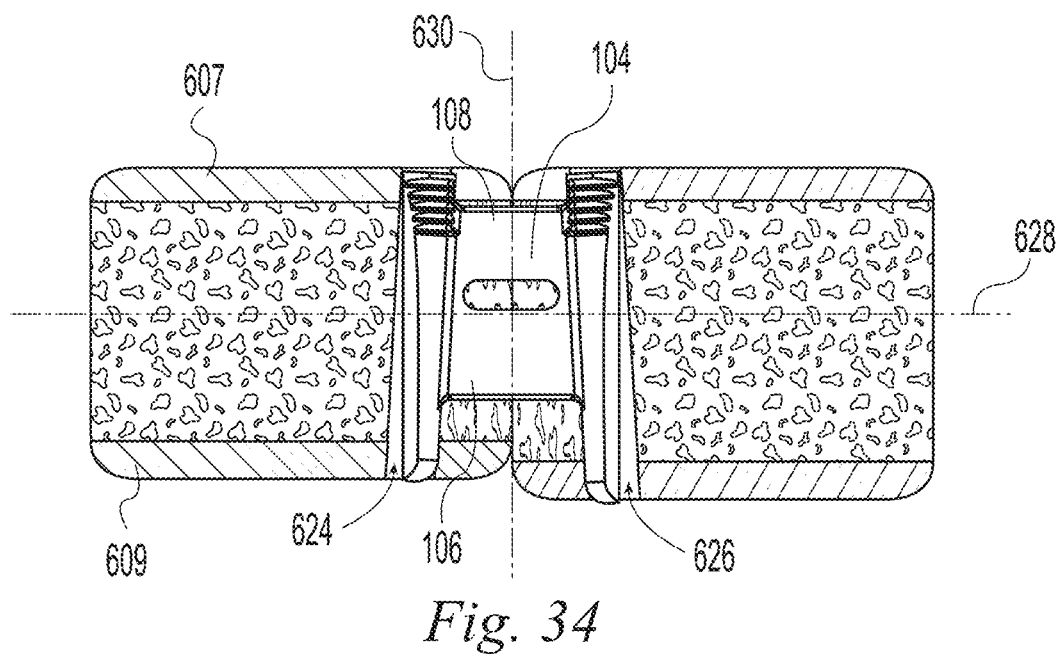

Referring to FIGS. 33 and 34, the inboard gaps 620, 622 diminish as the fastener is advanced until at some point in the fastener's travel, the fastener leg inboard surfaces 128, 130 contact the inboard bone hole walls. Since the inboard surfaces 128, 130 diverge at the same angle as the bone holes 610, 612, the fastener leg inboard surfaces 128, 130 contact the bone all along the length of the portions of the legs that have been inserted. Further advancing the fastener will compress the bone between the fastener legs uniformly along the fastener legs proximally to distally. In other words, as the fastener is further advanced, the bone is compressed between the fastener legs normal to the insertion direction the same amount at every point along the fastener legs proximally to distally. For bones having a longitudinal axis 628 normal to the insertion direction 630, the bone portions will be compressed axially relative to the longitudinal axis 628. The amount of compression can be tailored by setting the spacing of the inboard surfaces of the bone holes 610, 612 relative to the fastener leg inboard surfaces 128, 130. With the inboard bone hole surfaces further apart, the inboard fastener surfaces will contact the bone holes earlier in the fastener's travel and further advancing the fastener to a final resting position will cause relatively more compression. Alternatively, with the inboard bone hole surfaces closer together, the inboard leg surfaces will contact the bone holes later in the fastener's travel and further advancing the fastener to the same final resting position will cause relatively less compression. Preferably the fastener 100 is seated with the trailing ends of the fastener legs flush with or below the bone surface to reduce irritation of surrounding tissues. Preferably the fastener 100 is seated with the trailing end 108 of the body below flush and more preferably below the proximal cortex 607 to allow for cortical healing above the fastener body 104. To remove the fastener, it is pulled proximally. The sharpened trailing edge of the body 104 aids in passing the body through any bone that has grown over the body 104. Preferably the leading end 106 of the body stays inside the bone and more preferably the leading end 106 is above the distal cortex 609 to preserve bone strength.

Figure 35:
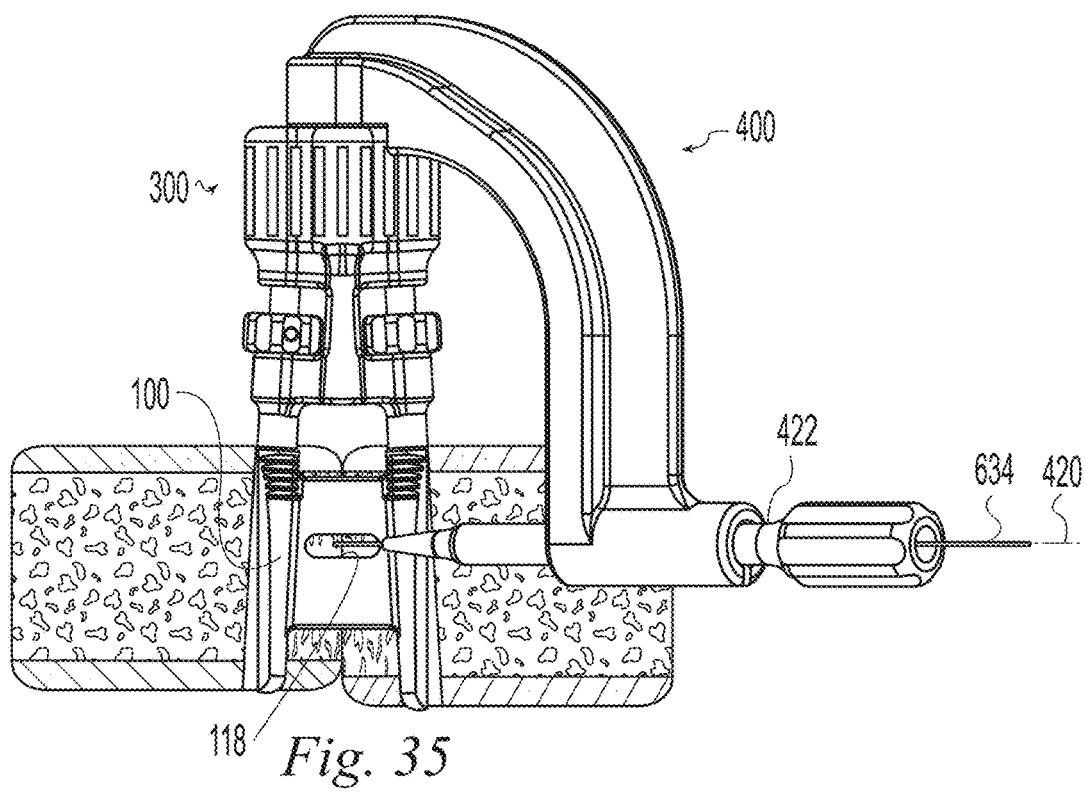
Figure 36:
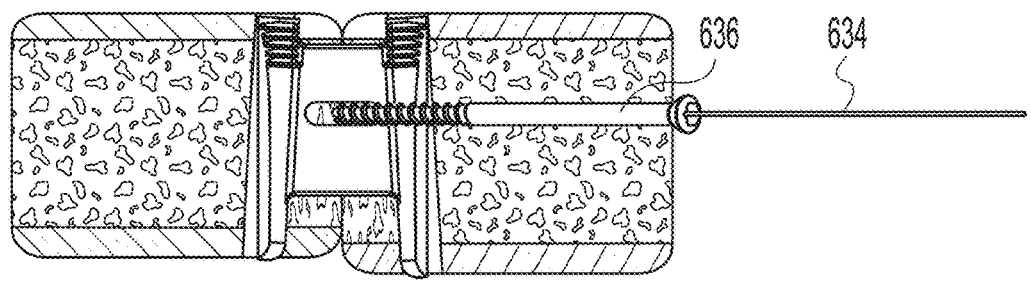
Figure 37:
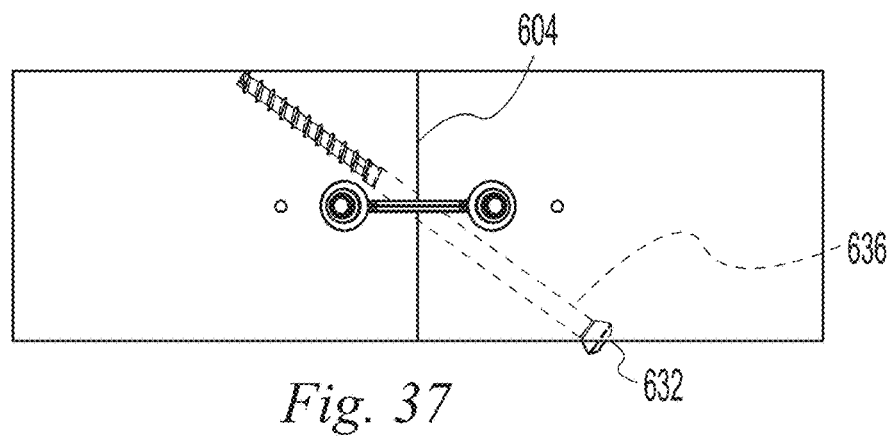

Referring to FIGS. 35-37, the cross fixation guide 400 is mounted to the inserter 300 which is attached to the fastener 100. The cross fixation guide 400 is pivoted relative to the inserter 300 to direct the cross fixation axis 420 in a desired direction. For example, it may be pivoted to align with a desired entry point on the bone 632. The rotation stops guarantee that the axis 420 is not angled so acutely as to prevent passage of a fixation member through the fastener aperture 118. The sleeve 422 is translated axially to position the sleeve close to the bone entry point 632 to stabilize a guide wire 634 as it is inserted through the sleeve, into the bone, and through the aperture 118. A fixation screw 636 is advanced over the guide wire 634 into the bone and through the aperture 118. The guide wire 634 is then removed. Preferably the screw 636 is sized and positioned for bi-cortical fixation. Preferably the screw passes through both bone portions to further stabilize the interface 604.

The implants, instruments and methods of examples of the invention may be used at many different locations within a patient to secure bone portions relative to one another and may further be used to form various constructs as shown in the illustrative examples of FIGS. 38-44. While illustrative, these examples are not comprehensive and it will be apparent to one skilled in the art that these implants, instruments, and methods may be used anywhere two bone portions are to be secured. The size and proportion of the fastener may be varied to suit a particular anatomical location.

Figure 38:
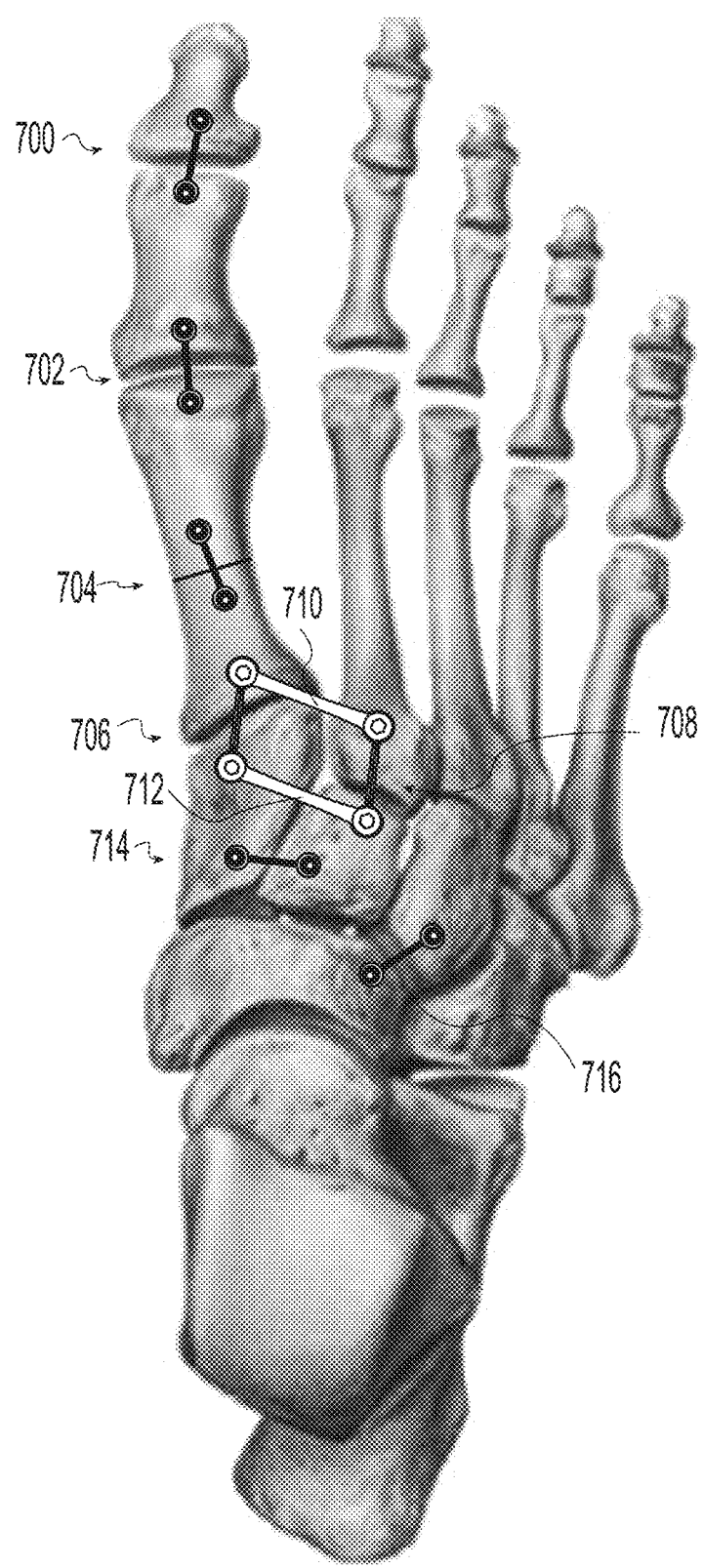
FIGS. 38-44 illustrate examples of surgical applications for the implant of FIG. 1.

Referring to FIG. 38, a human foot illustrates various examples of applications for the invention. A phalangeal fusion is indicated at 700. A metatarsophalangeal fusion is indicated at 702. A fusion of a midshaft fracture or osteotomy is indicated at 704. Metatarsocuneiform fusions are indicated at 706 and 708. In this example, joining elements 710, 712 have been attached between separate fasteners to form a construct in a lisfranc procedure. For example, the joining elements 710, 712 may be attached with screws threaded into the sockets in the proximal ends of the fastener legs. The joining elements 710, 712 may be rigid or flexible depending on the amount of constraint desired. Tarsal fusions are indicated at 714 and 716.

Figure 39:
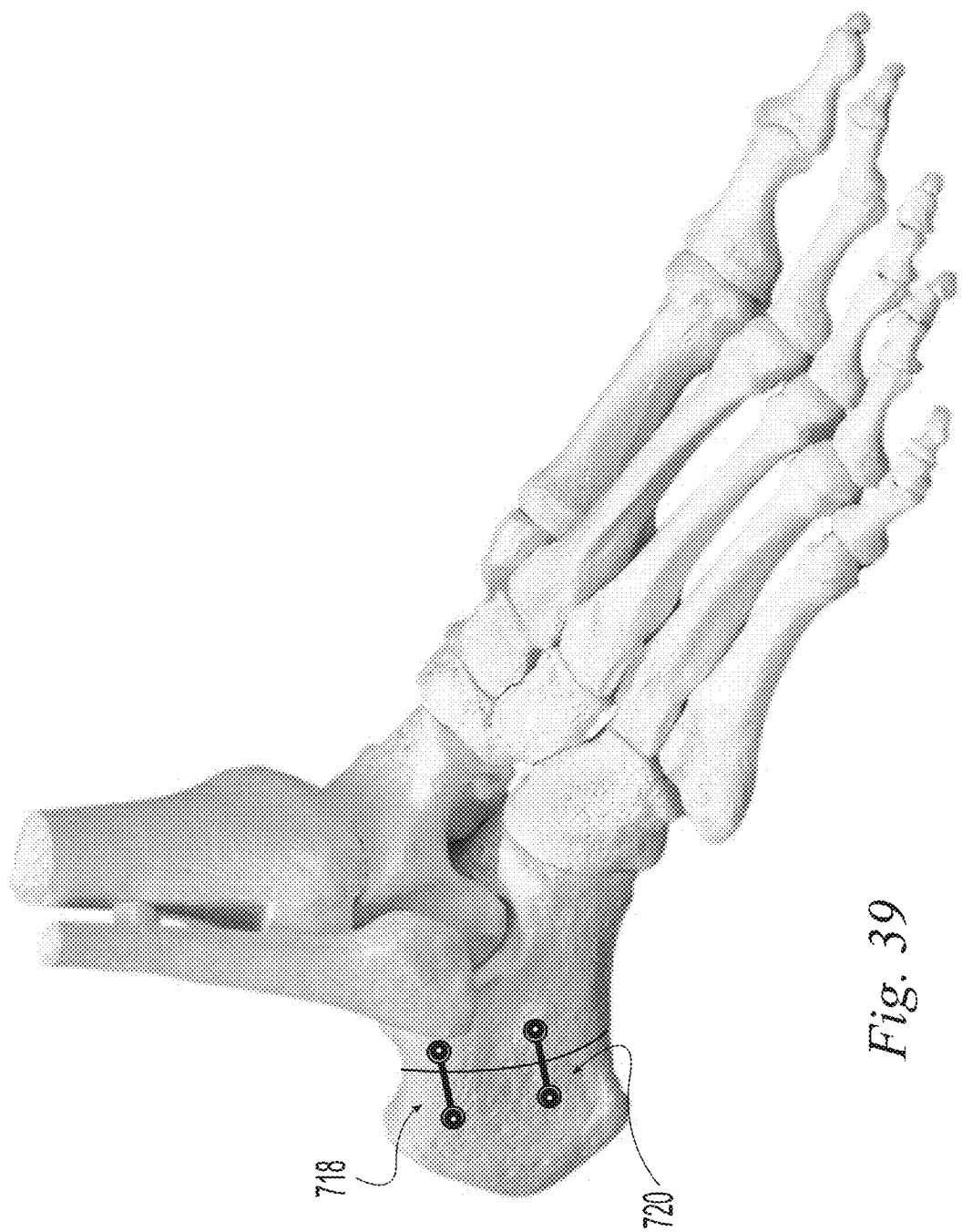

Referring to FIG. 39, a calcaneal osteotomy has been fixed using fasteners according to one example of the invention at 718 and 720.

Figure 40:
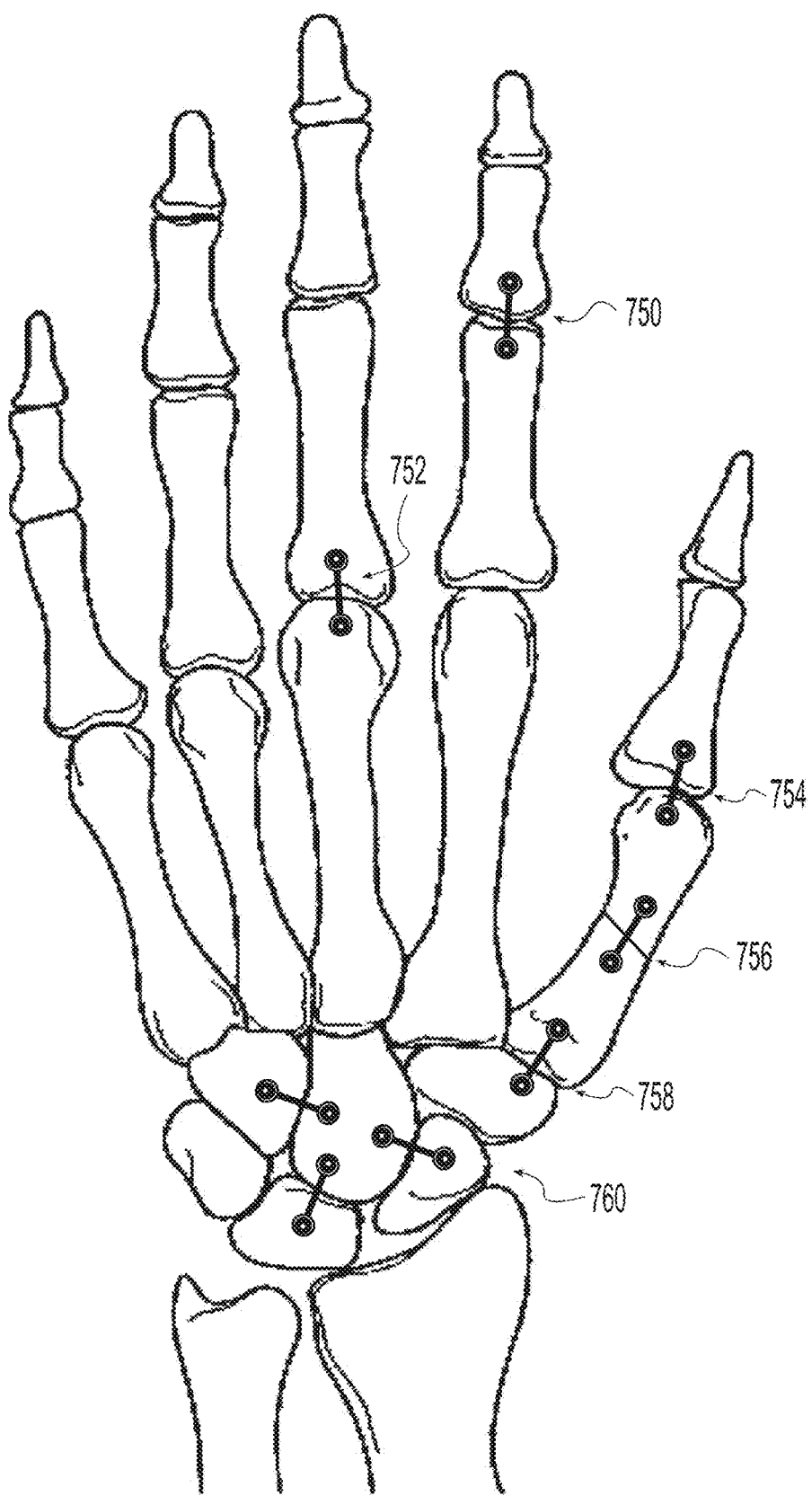

Referring to FIG. 40, applications in the human hand are illustrated similar to those shown for the foot. For example, these may include phalangeal fusion 750, metacarpophalangeal fusion 752 and 754, midshaft fusion 756, metacarpocarpal fusion 758, and carpal fusion 760.

Figure 42:
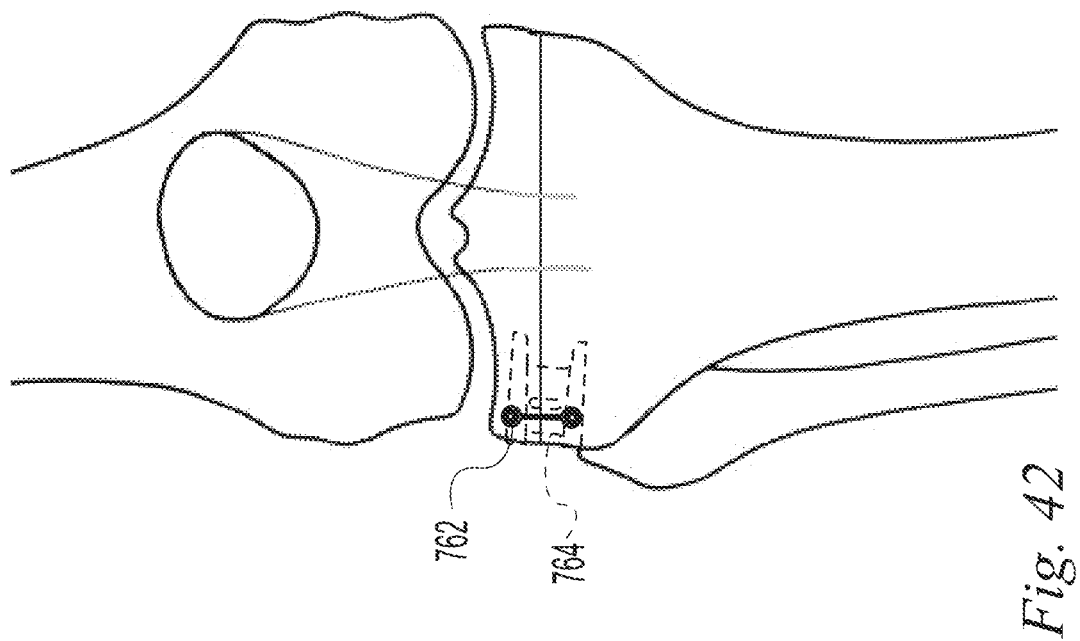
Figure 41:
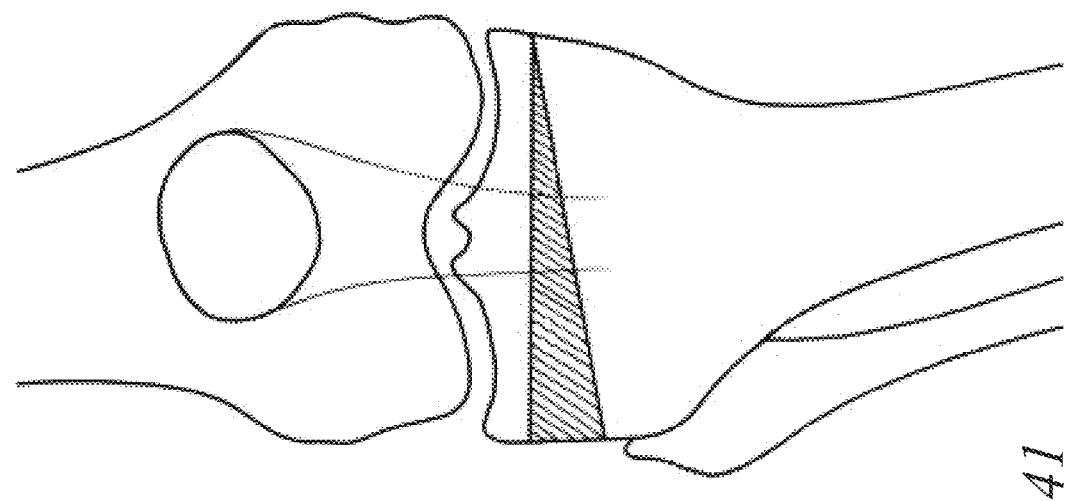

Referring to FIGS. 41 and 42, a closing wedge tibial osteotomy is illustrated in which the closed wedge is fixed with one or more of an anteriorly 762 and/or laterally 764 placed fastener according to one example of the invention.

Figure 44:
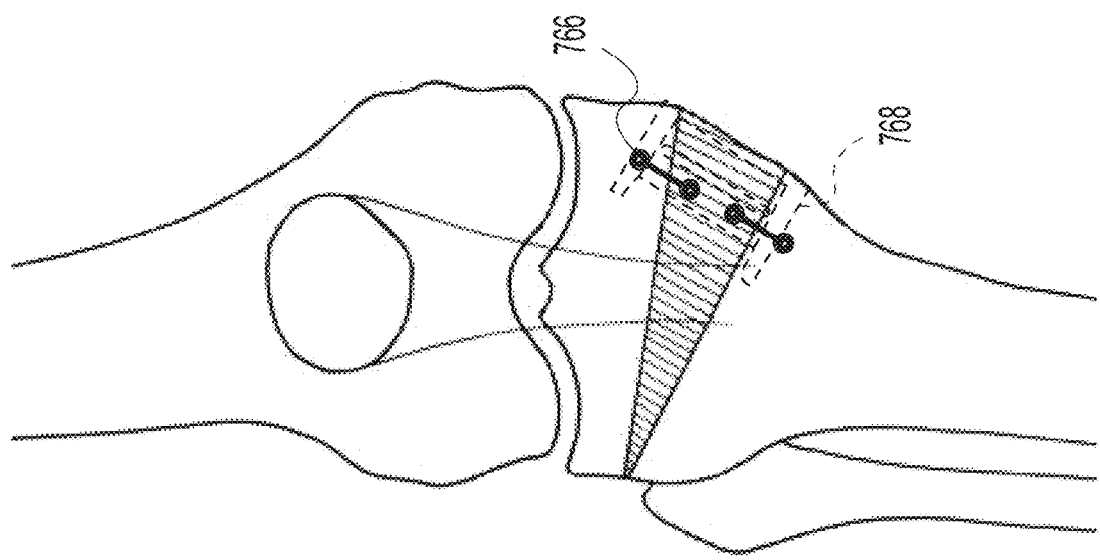
Figure 43:
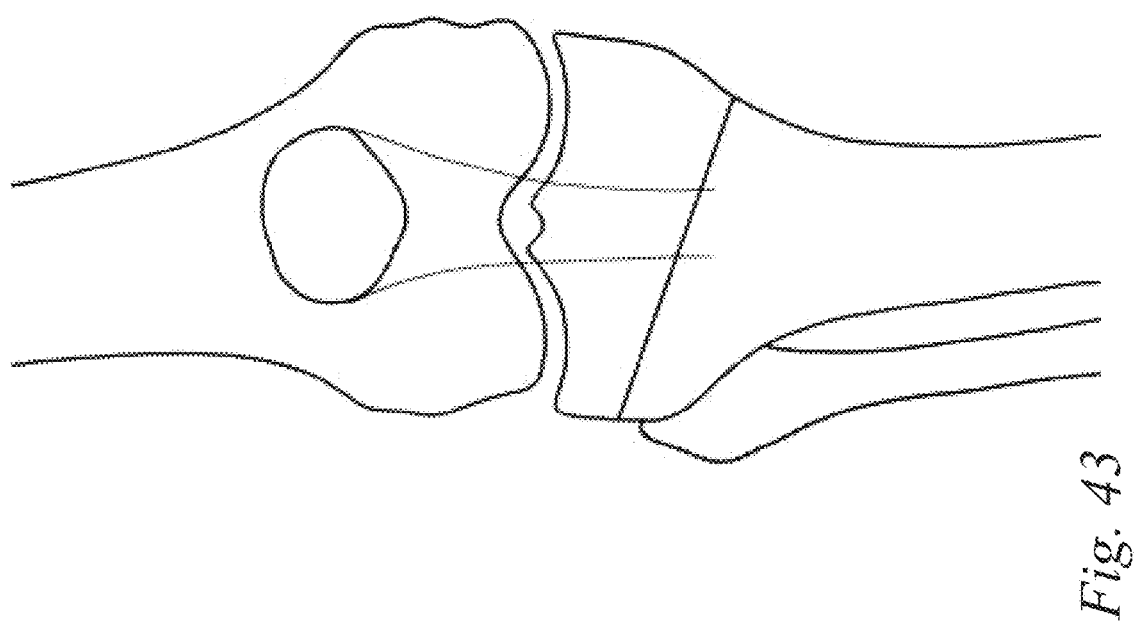
Figure 46:
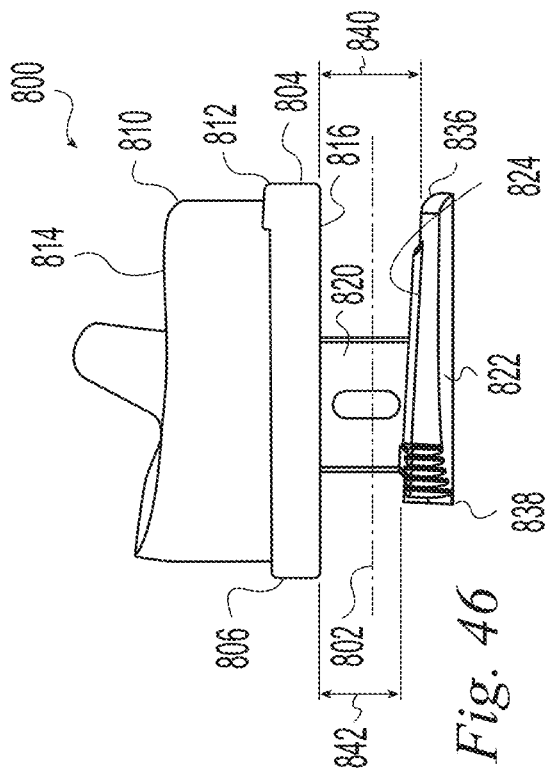
FIG. 46 is a side elevation view of the implant of FIG. 45.
Figure 47:
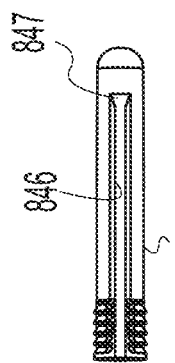
FIG. 47 is a top plan view of component 822 of the implant of FIG. 45.
Figure 45:
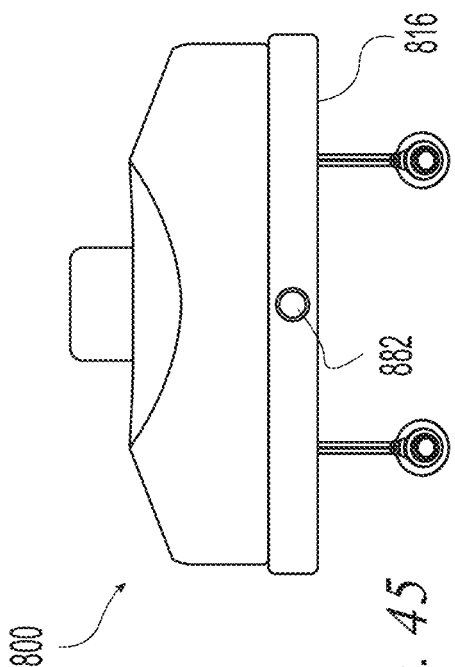
FIG. 45 is a front elevation view of an implant according to one example of the invention.
Figure 53:
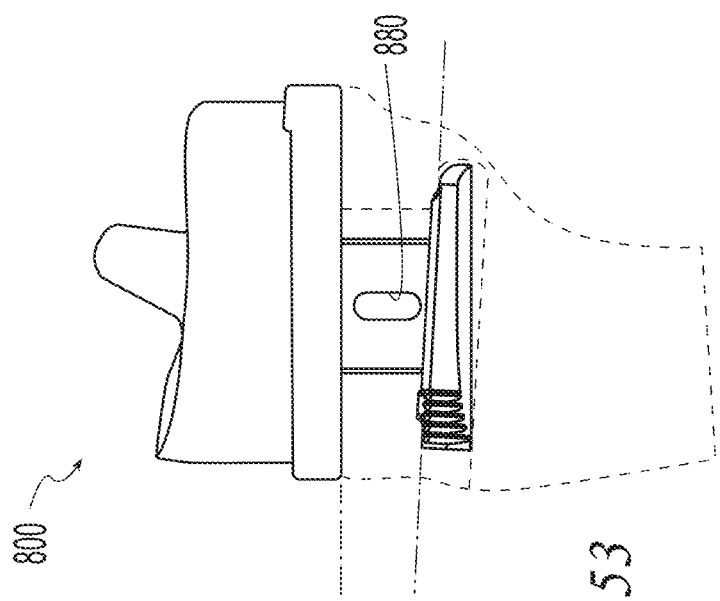
FIG. 53 is a side elevation view of the implant of FIG. 45 mounted on a bone.

Referring to FIGS. 43 and 44, an opening wedge tibial osteotomy is illustrated in which a graft is fixed into the opened wedge with one or more of an anteriorly 766 and/or medially 768 placed fastener according to one example of the invention. For illustration purposes, the medial fastener 768 is proportioned so that the fastener legs are inserted into tibial bone on either side of the graft.

In addition to securing two bone portions, it may be desirable to secure a spacer such as an articulating surface or fusion implant to a bone. For example, it is common practice to replace one or more of the articular surfaces of a diseased or injured skeletal joint to restore anatomic motion and/or reduce pain. Such joint replacement procedures may replace for example a discrete diseased portion of the joint as in a resurfacing procedure or in a uni-compartmental arthroplasty procedure. Joint replacement procedures may replace the entire articulating surface of one bone of a joint leaving the other bone, or bones, in their natural state such as for example in a hemi-arthroplasty procedure. Joint replacement procedures may replace all of the articulating surfaces at a joint as in, for example, a total joint arthroplasty. Often the implants utilized include a spacer having a base plate and/or a stem to anchor the implant to the underlying bone and may include surfaces for cementitious or osseous integration for enhanced fixation. Joint arthroplasty has been proposed for use at the shoulder, elbow, wrist, hand, and finger joints of the upper extremity. It has likewise been proposed for use at the hip, knee, ankle, foot, and toe joints of the lower extremity. Joint arthroplasty has been proposed for use between adjacent vertebrae of the spine. Joint implants may include articulating spacers to facilitate motion between bones or they may include stationary spacers intended to cause joint fusion with a desired bone spacing. FIGS. 45-50 illustrate an example of an implant 800 for resurfacing at least a portion of an articulating end of a bone adjacent a skeletal joint in one example of the invention. The form of the articular surface of the implant may take any form suitable for a particular joint in the body.

In the example of FIGS. 1A-9, features of the implant inserted into opposing bone portions cause compression of one bone portion against another bone portion. In the example of FIGS. 45-57, features of the implant cause compression of a portion of the implant against an external surface of a bone such as a natural or prepared surface. For example, a first portion of the implant contacts an external surface of the bone and a second portion of the implant is inserted into the bone to cause compression of the first portion of the implant against the external surface of the bone. These features may be incorporated in an implant suitable for any skeletal joint.

By way of example, FIGS. 45-50 illustrate an implant 800 in the form of a tibial prosthesis that provides an articular surface on the proximal end of a tibia after it has been prepared by removing the natural articular surface to create a planar surface. The implant 800 includes a spacer or articular portion that is positioned on a surface of a prepared tibia and an anchor portion including a leg that is inserted into the tibial bone. The implant includes an insertion axis 802 extending between a leading end 804 and a trailing end 806. In the illustrative example of FIGS. 45-50, the articular portion comprises a separate bearing component 810 and a tray component 812 removably joined together. Alternatively, the bearing component and tray component may be a single unitary construct. The bearing component 810 has an upper bearing surface 814 for articulation with an opposing bone or implant component (not shown). The tray component 812 has a lower bone engaging surface 816 that rests on the surface of the prepared tibia. In the example of FIGS. 45-50, the lower surface 816 is planar and parallel to the insertion axis. The lower surface 816 may include various bone ingrowth or cement bonding features as are known in the art. The lower surface 816 may include roughened textures, spikes, tabs, posts, and/or other features for immediate mechanical engagement of the bone surface.

A leg 822 is joined to the lower bone engaging surface of the spacer for insertion into the tibia. In the illustrative example of FIGS. 45-50, the leg is joined to the spacer by way of an intermediate body 820. The anchor portion includes the body 820 joined to and extending from the lower surface 816 and the leg 822 joined to the distal end of the body 820. In the illustrative example of FIGS. 45-50, the body 820 and leg 822 are configured generally as shown and described relative to the example of FIGS. 1A-9 with the second leg of FIGS. 1A-9 being replaced by the spacer. As with the example of FIGS. 1A-9, the inboard surface 824 of the leg faces the insertion axis 802 and extends from a leading end 836 to a trailing end 838 and the inboard surface 824 is spaced from the lower surface 816 a leading distance 840 near the leading end and a trailing distance 842 near the trailing end. In the example of FIGS. 45-50, the leading distance 840 is greater than the trailing distance 842 so that the lower surface 816 and inboard surface 824 diverge in the leading direction defined by the leading end. When the implant 800 is inserted with the lower surface 816 adjacent a prepared tibial surface and the leg in a hole formed in the tibial bone, the implant will be secured against lifting off of the bone. Increasing insertion depth will result in increasing compression, as described relative to the example of FIGS. 1A-9, of the lower surface 816 against the prepared tibial surface due to the divergence of the lower surface and the leg.

Optionally, the leg may be removably attached to the spacer. The leg may be provided as a plurality of legs, the plurality of legs being interchangeable mountable relative to the spacer to provide a selectable size or shape of first leg. The leg may be engaged in sliding relationship to facilitate independent positioning of the articular component on the bone and adjusting of the compression created by the anchor component. For example, referring to FIGS. 47 and 48, the leg 822 may include a lengthwise slot 846 able to receive an enlarged edge 848 of the body. The leg 822 may slide lengthwise relative to the body but is prevented from moving distally away from the body 820 while the enlarged edge 848 is engaged with the slot 846. The enlarged edge may take any form known in the art for producing a mechanism that slides in one direction but is constrained in a transverse direction. Examples may include but are not limited to a dovetail, spline, key hole, key and keyway, or other form. The slot 846 may extend the full length of the leg 822 or only partway. The leg 822 may be trapped on the body 820 or it may be removable and replaceable in one or both of the leading direction or trailing direction. In the example of FIGS. 45-50, the leg 822 is slotted from the trailing end 838 partway toward the leading end 836. The leg 822 may be removed from the body by sliding it in the leading direction as seen in FIG. 48. The leading end of the slot 846 will abut the body 820 to prevent it from being removed in the trailing direction as seen in FIG. 49. The position of the leg 822 shown in FIG. 49 is the initial insertion position. FIG. 50 illustrates the leg having been driven forward to a subsequent position that will increase the compression of the lower surface 816 against the bone.

Figure 51:
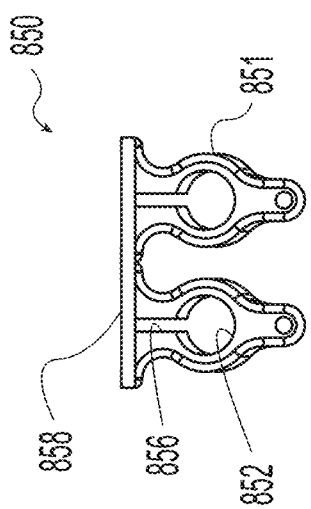
FIG. 51 is a front elevation view of an example of a hole forming guide for the implant of FIG. 45.
Figure 52:
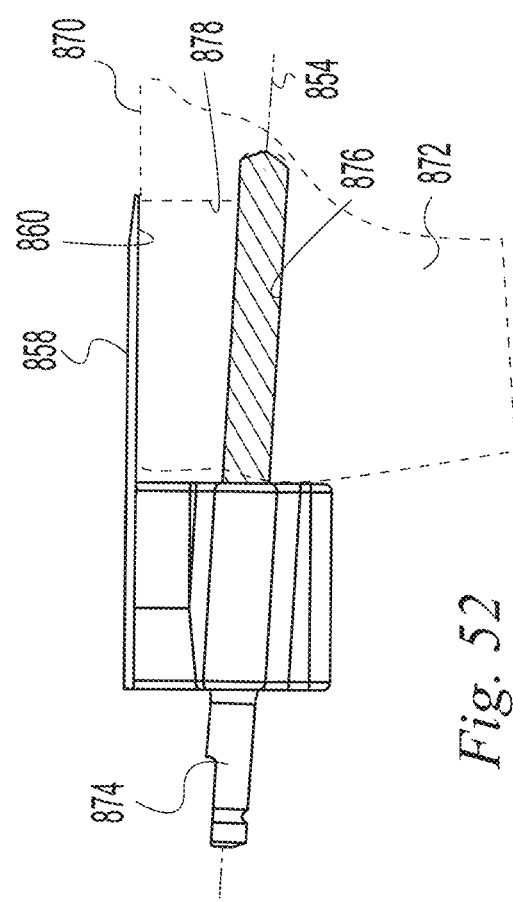
FIG. 52 is a side elevation view of the guide of FIG. 51.

FIGS. 51 and 52 illustrate a hole forming guide 850 having a guide body 851. The guide is similar to that of FIGS. 10-14 including holes 852 having axes 854 for guiding a punch, drill or the like to form a bone hole for receiving the leg 822 and slots 856 for guiding a saw, chisel, or the like to form a bone slot for receiving the body 820. The guide 850 includes a probe 858 having a probe lower surface 860 engageable with the bone surface on which the tray lower surface 816 will rest to orient the holes 852 and slots 856 relative to the bone surface. In the example of FIGS. 51 and 52, the hole axes 854 diverge from the probe lower surface 860 at an angle equal to the divergence of the tray lower surface 816 and leg inboard surface 824. As described relative to the example of FIGS. 1A-9, the equal divergence of the hole and leg results in uniform compression over the length of the leg.

In use, the guide 850 is positioned with the probe lower surface 860 resting on the planar cut surface 870 of the tibia 872 and the guide body 851 abutting the anterior of the tibia as shown in FIG. 52. A drill 874, for example, is guided in the guide hole 852 to form a bone hole 876. A saw (not shown), for example, is guided in the slot 856 to form a bone slot 878 intersecting the bone hole 876 and the cut surface 870 of the tibia. The guide 850 is removed. Referring to FIG.

53, the implant 800, is pressed in the leading direction with the lower surface of the tray 816 in contact with the cut surface 870, the body 820 in the slot 878, and the leg 822 in the bone hole 876. As the implant is driven forward, the leg will engage the wall of the bone hole as described relative to the example of FIGS. 1A-9. As the implant tray 812 reaches its final position on the tibia it is compressed down against the tibial surface. Where an optional separate sliding leg 822 is provided, the tray 812 may be positioned at a desired location on the tibia and the leg 822 then driven to compress the tray 812 against the bone. This modular construction allows for independent positioning and compression. For example, where the lower bone engaging surface includes a fixation feature projecting from it, the lower bone engaging surface may first be engaged with the bone in a first direction transverse to the surface and then, without shifting the bone engaging surface across the bone, the leg may be advanced in a second direction transverse to the first direction to compress the bone engaging surface against the bone. A crossing screw may be placed through the optional aperture 880 if desired as described relative to the example of FIGS. 1A-9 such as by using the cross fixation guide 400 of FIG. 19. In another example, the optionally separate sliding leg may be positioned as shown in FIG. 49, with the leading end of the body 820 abutting the leading end 847 of the slot 846. As the implant is driven forward, e.g. by engaging a driver with a threaded hole 882 in the trailing end of the tray (FIG. 45), the abutting body 820 drives the leg 822 forward with it. Once the tray 812 is positioned as desired, a driver may be engaged with the trailing end of the leg 822 to drive the leg to compress the implant against the bone. To remove the implant 800, a removal tool, e.g. a slap hammer, may be engaged with the trailing end of the leg 822 and the leg withdrawn to reduce the compression and allow the implant to be removed. A driver or removal tool may engage the leg 822 via a threaded socket such as that shown in FIG. 9.

Figure 54:
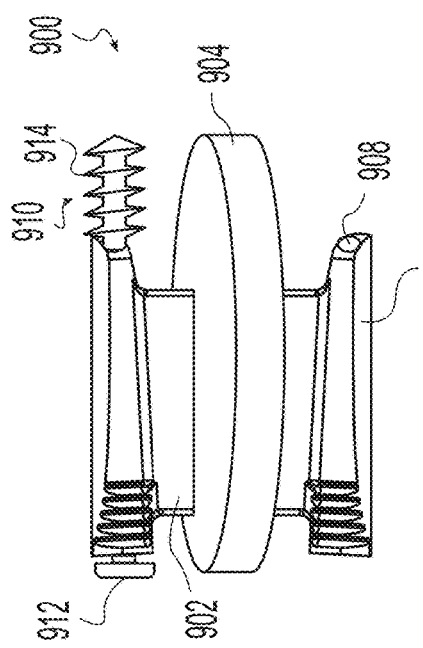
FIG. 54 is a side elevation view of an implant according to one example of the invention.

FIG. 54 illustrates another example of an implant 900 similar to that of FIGS. 1A-9. In the example of FIG. 54, the body 902 includes a spacer 904 that may be placed between bone portions to maintain them a desired distance apart and anchor portions, as described relative to the example of FIGS. 45-50, positioned on opposite sides of the spacer 904. The implant 900 of FIG. 54 is suitable, for example, for spacing and securing adjacent bone portions while they fuse together during healing. Examples of applications for such an implant include fusing adjacent vertebrae of the spine, joint fusions at other locations, osteotomy fusions, and the like where it is desired to fill a natural or surgically created gap between the bone portions. The spacer 904 may have planar, parallel opposing sides as shown or they may be shaped to fit the contours of the adjacent bone and/or to fill an angled gap. In the example of FIG. 54, the legs 906 include a through hole 908 that may receive a screw 910 axially. In the example of FIG. 54, only one screw is shown but one may be provided in both legs or not at all. The screw has a trailing head 912 and a leading thread 914. When the screw 910 is rotated, the threads engage the wall of the bone hole and the head abuts the trailing end of the leg to pull the leg 906 and thus the implant 900 forward into engagement with the bone. The screw 910 allows the implant 900 to be driven smoothly without impact forces. The screw also prevents the implant 900 from translating backward. The screw may be permanently trapped within the implant or it may be removably engaged. For example, the leg 906 may have a longitudinal slot through which the screw may be moved laterally to be engaged with or disengaged from the leg 906.

Figure 55:
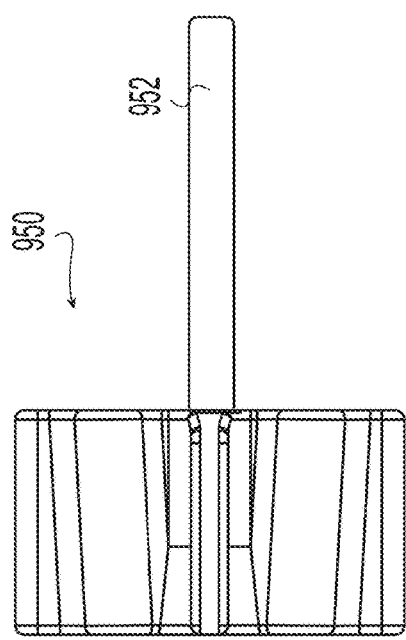
FIG. 55 is a side elevation view of an example of a hole forming guide for the implant of FIG. 54.

FIG. 55 illustrates a hole forming guide 950 similar to that of FIGS. 10-14 but having an additional probe 952 with a thickness equal to that of the spacer 904 and which is inserted between the bone portions to position them in the proper orientation relative to the guide 950.

Figure 57:
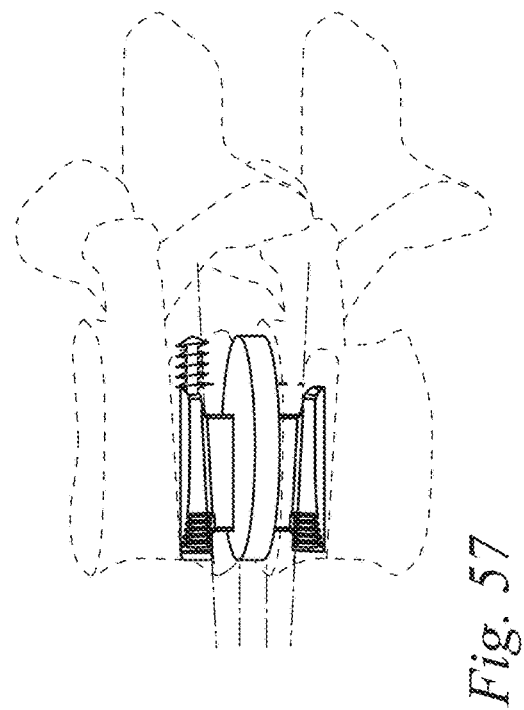
FIG. 57 is a side elevation view of the implant of FIG. 54 mounted to adjacent bones.
Figure 56:
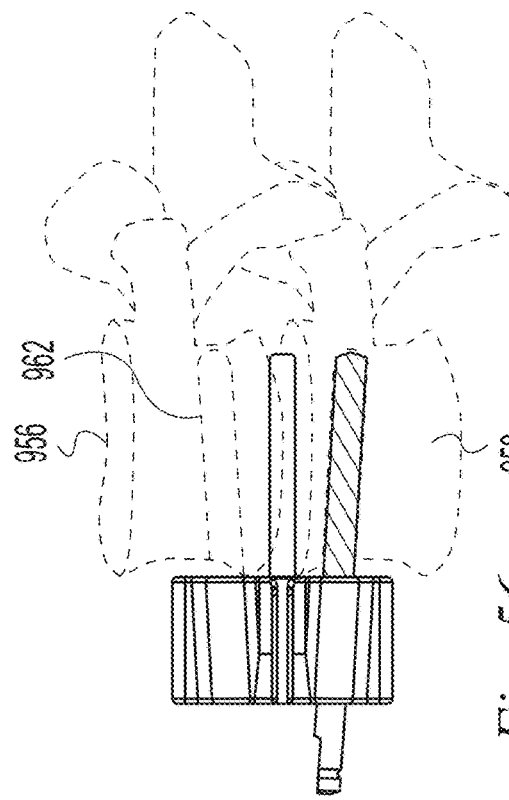
FIG. 56 is a side elevation view of the hole forming guide of FIG. 55.

FIGS. 56 and 57 illustrate an interbody fusion procedure using the guide 950 and implant 900. The guide is positioned with the probe 952 between the vertebrae 956, 958 and a hole 962 is formed in each bone portion. The guide 950 is removed and the implant 900 is inserted so that each bone portion is compressed against one of the opposing sides of the spacer 904.

Several illustrative examples have been shown. The various features of the different examples may be combined or substituted among the examples within the scope of the invention. For example, the independently sliding leg shown in the example of FIG. 45-50 may be used with the example of FIGS. 1A-9 or the example of FIG. 54. Likewise, the longitudinal screw of FIG. 54 may be used with the example of FIGS. 1A-9 or the example of FIG. 45-50. Similarly, the threaded inserter 300 of FIGS. 15-18, the cross fixation guide 400 of FIG. 19, or the flexible member 502 of FIGS. 23-25 may be used with the example of FIGS. 45-50 or the example of FIG. 54.

Following are further examples of the invention.

1. A bone fastener stabilizing a first bone portion relative to a second abutting bone portion, the first bone portion having a first preformed hole extending distally from a surface of the first bone portion into the first bone portion and defining a first hole axis and the second bone portion having a second preformed hole extending distally from a surface of the second bone portion into the second bone portion and defining a second hole axis, the first and second hole axes diverging from one another distally, the construct comprising:
  a bone fastener having an insertion axis along which the fastener moves as it is inserted into or removed from a bone; a body; a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance; the bone fastener first leg being inserted into said first preformed hole and the bone fastener second leg being inserted into said second preformed hole.

2. The bone fastener of example 1 wherein the first leading distance is greater than the first trailing distance.

3. The bone fastener of example 2 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

4. A bone fastener comprising:
an insertion axis along which the fastener moves as it is inserted into or removed from a bone;
a body having a generally planar configuration having opposed planar sides spaced apart a body thickness, the body extending between a distal body leading end and a proximal body trailing end, the body leading end and the body trailing end being spaced from one another longitudinally relative to the insertion axis, the opposed planar sides converging toward the body trailing end to define a trailing edge having a trailing edge thickness less than the body thickness;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and
a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance.

5. The bone fastener of example 4 wherein the first leading distance is greater than the first trailing distance.

6. The bone fastener of example 5 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

7. The bone fastener of example 4 wherein the trailing end of each of the first and second legs extends proximally beyond the trailing edge of the body.

8. A bone fastener construct stabilizing a first bone portion relative to a second abutting bone portion, the construct comprising:
an insertion axis along which the fastener moves as it is inserted into or removed from a bone;
a body and an aperture through the body, the aperture having a length and a width, the aperture length being greater than the aperture width, the aperture length being oriented transverse to the insertion axis;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and
a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance.

9. The bone fastener construct of example 8 wherein the first leading distance is greater than the first trailing distance.

10. The bone fastener construct of example 9 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

11. The bone fastener construct of example 8 wherein the trailing end of each of the first and second legs extends beyond the trailing edge of the body.

12. The bone fastener construct of example 8 further comprising an elongate fixation member positioned within the aperture and engaging at least one of the first and second bone portions.

13. The bone fastener construct of example 12 wherein the elongate fixation member engages both the first and second bone portions.

14. The bone fastener construct of example 8 further including a guide having a guide axis, the guide being mounted to the fastener in rotating relationship, the guide being rotatable between a plurality of positions in which the guide axis intersects the aperture.

15. The bone fastener construct of example 14 wherein the aperture defines a central axis parallel to the insertion axis, the guide being mounted for rotation about the central axis between a plurality of rotated positions, the guide axis intersecting the central axis in each of the plurality of rotated positions.

16. The bone fastener construct of example 14 further comprising an elongate fixation member having a longitudinal axis and a width measured normal to the longitudinal axis, wherein the guide and fastener define at least one stop that limits the rotation of the guide relative to the fastener in at least one direction to an included angle between the guide axis and the aperture having a value corresponding to a projected length of the aperture along the guide axis equal to or greater than the width of the fixation member.

17. A bone fastener comprising:
an insertion axis along which the fastener moves as it is inserted into or removed from a bone;
a body having a distal body leading end and a proximal body trailing end, the body leading end and the body trailing end being spaced from one another longitudinally relative to the insertion axis;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being greater than the first trailing distance; and a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance, wherein the trailing end of each of the first and second legs extends proximally beyond the trailing end of the body.

18. The bone fastener of example 17 wherein the leading end of each of the first and second legs extends distally beyond the leading end of the body.

19. The bone fastener of example 17 wherein the body has a generally planar configuration having opposed planar sides spaced apart a body thickness, the body extending between the body leading end and the body trailing end, the opposed planar sides converging toward the body trailing end to define a trailing edge having a trailing edge thickness less than the body thickness.

20. The bone fastener of example 19 wherein the trailing edge is operable to cut through bone to aid in extraction of the fastener after bone has grown over the trailing edge.

21. The bone fastener of example 19 wherein the opposed planar sides converge toward the body leading end to define a leading edge having a leading edge thickness less than the body thickness.

22. The bone fastener of example 21 wherein the leading edge is operable to cut through bone to aid in insertion of the fastener.

23. The bone fastener of example 22 wherein the leading end of each of the first and second legs extends distally beyond the leading edge of the body.

24. The bone fastener of example 17 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

25. A bone fastener comprising:
an insertion axis along which the fastener moves as it is inserted into or removed from a bone;
a body;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being greater than the first trailing distance; and
a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance;
wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

26. A bone fastener operable to stabilize a first bone portion relative to a second abutting bone portion, the bone fastener comprising:
an insertion axis along which the fastener moves as it is inserted into or removed from a bone;
a body having a distal leading end and a proximal trailing end, the body leading end and the body trailing end being spaced from one another longitudinally relative to the insertion axis;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and
a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance;
wherein the trailing end of each of the first and second legs extends proximally beyond the trailing end of the body, the fastener being operable upon insertion of the first leg into the first bone portion and the second leg into the second bone portion to translate the first and second bone portions in a direction transverse to the insertion axis.

27. The bone fastener of example 26 wherein the first leading distance is greater than the first trailing distance.

28. The bone fastener of example 27 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

29. A method of stabilizing a first bone portion relative to a second abutting bone portion, the method comprising:
providing a bone fastener having an insertion axis; a body; a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance;

preforming a first hole from a surface of the first bone portion distally into the first bone portion, the first hole defining a first hole axis;

preforming a second hole from a surface of the second bone portion distally into the second bone portion, the second hole defining a second hole axis, the first and second hole axes diverging from one another distally; and inserting the bone fastener with the first leg in the first hole and the second leg in the second hole.

30. The method of example 29 wherein the first leading distance is greater than the first trailing distance.

31. The method of example 30 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

32. The method of example 29 wherein the body has a distal leading end and a proximal trailing end, the body leading end and the body trailing end being spaced from one another longitudinally relative to the insertion axis, the trailing end of each of the first and second legs extending proximally beyond the trailing end of the body and the step of inserting the fastener comprises inserting the trailing end of the body below the surface of at least the first bone.

33. The method of example 29 wherein the fastener body includes an aperture through the body, the method further comprising inserting an elongate fixation member through the aperture and into engagement with at least one of the first and second bone portions.

34. The bone method of example 33 wherein inserting an elongate fixation member comprises positioning the elongate fixation member simultaneously within the aperture and in engagement with both the first and second bone portions.

35. The method of example 29 further comprising:
providing a guide having a guide axis;
mounting the guide to the fastener;
aligning the guide axis with the aperture; and
guiding a member with the guide along the guide axis and into the aperture.

36. The method of example 35 wherein the guide is mounted for rotation about the central axis between a plurality of rotated positions, the guide axis intersecting the aperture in each of the plurality of rotated positions.

37. The method of example 35 further comprising:
providing an elongate fixation member having a longitudinal axis and a width measured normal to the longitudinal axis;
providing a stop that limits the rotation of the guide relative to the fastener to an included angle between the guide axis and the aperture having a value corresponding to a projected length of the aperture along the guide axis equal to or greater than the width of the fixation member; and
positioning the guide in one of the plurality of rotated positions and guiding an elongated fixation member to intersect the aperture.

38. The method of example 29 further comprising:
removing the bone fastener by propelling a trailing edge of the bone fastener through bone that has grown over the trailing edge.

39. The method of example 38 wherein the body has a generally planar configuration having opposed planar sides spaced apart a body thickness, the body extending between a body leading end and a body trailing end, the opposed planar sides converging toward the body trailing end to define the trailing edge having a trailing edge thickness less than the body thickness 40. The method of example 29 wherein inserting the bone fastener causes relative translation of the first and second bone portions transverse to the insertion axis.

41. The method of example 40 wherein inserting the bone fastener does not create a relative bending moment between the first and second bone portions.

42. The method of example 29 wherein inserting the bone fastener creates compression between the first and second bone portions.

43. The method of example 42 wherein inserting the bone fastener does not create a relative bending moment between the first and second bone portions.

44. The method of example 42 wherein inserting the bone fastener creates uniform compression of the bone between the fastener legs.

45. The method of example 29 wherein inserting the bone fastener comprises:
inserting the bone fastener with the first leg in the first hole and the second leg in the second hole to a first position in which there is a gap between inboard side of the first leg and the inboard wall of the first hole, and a gap between the inboard side of the second leg and the inboard wall of the second bone hole; and
inserting the bone fastener further to a second position in which the inboard side of the first leg and the inboard wall of the first hole are in contact and the inboard side of the second leg and the inboard wall of the second hole are in contact.

46. The method of example 45 further comprising:
inserting the bone fastener further to a third position in which the inboard side of the first leg and the inboard side of the second leg compress bone between them.

47. The method of example 46 wherein the inboard side of the first leg and the inboard side of the second leg provide uniform compression at all positions between the legs normal to the insertion axis.

48. A method of removing a fastener from a bone, the method comprising propelling a trailing edge of the fastener through bone that has grown over the trailing edge.

49. The method of example 48 wherein the fastener has an insertion axis; a body having a generally planar configuration having opposed planar sides spaced apart a body thickness, the body extending between a body leading end and a body trailing end, the opposed planar sides converging toward the body trailing end to define the trailing edge having a trailing edge thickness less than the body thickness; a first leg connected to the body; and a second leg connected to the body.

50. A method of stabilizing a first bone portion relative to a second abutting bone portion, the method comprising:
providing a bone fastener having an insertion axis along which the fastener moves as it is inserted into or removed from a bone; a body having a distal leading end and a proximal trailing end, the body leading end and the body trailing end being spaced from one another longitudinally relative to the insertion axis; a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance; wherein the trailing end of each of the first and second legs extends proximally beyond the trailing edge of the body; and
inserting the first leg into the first bone portion and the second leg into the second bone portion to translate the first and second bone portions in a direction transverse to the insertion axis.

51. The method of example 50 wherein the first leading distance is greater than the first trailing distance.

52. The method of example 51 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

53. A method of stabilizing a first bone portion relative to a second abutting bone portion, the method comprising:
providing a bone fastener having an insertion axis; a body having an aperture therethrough; a first leg connected to the body; and a second leg connected to the body;
inserting the fastener along the insertion axis into the first and second bone portions;
mounting a guide to the fastener in rotating relationship, the guide having a guide axis, the guide being rotatable between a plurality of positions in which the guide axis intersects the aperture;
rotating the guide relative to the fastener to one of the plurality of positions; and
guiding an elongate member with the guide into at least one of the bone portions and into the aperture.

54. The method of example 53 wherein the elongate member comprises a guidewire, the method further comprising:
inserting an elongate fixation member over the guidewire and into a final position in which the elongate fixation member is simultaneously positioned in the first bone portion, the aperture, and the second bone portion.

55. The method of example 53 further comprising:
providing an elongate fixation member having a longitudinal axis and a width measured normal to the longitudinal axis; and
providing a stop that limits the rotation of the guide relative to the fastener to an included angle between the guide axis and the aperture having a value corresponding to a projected length of the aperture along the guide axis equal to or greater than the width of the fixation member.

56. A bone fastener construct comprising:
a first bone fastener inserted into a first bone portion;
a second bone fastener inserted into a second bone portion; and
a first bridging member, separate from the first and second bone fasteners, connected to and extending between the first and second bone fasteners.

57. The bone fastener construct of example 56 further comprising a second bridging member, separate from the first and second bone fasteners, connected to and extending between the first and second bone fasteners.

58. The bone fastener construct of example 56 wherein at least one of the first and second bridging members is connected to at least one of the first and second fasteners with a connector received in an opening in a trailing end of the at least one of the first and second fasteners.

59. The bone fastener construct of example 56 wherein the bridging member is rigid and maintains the fasteners in a fixed spaced relationship.

60. The bone fastener construct of example 56 wherein the bridging member is flexible and permits relative motion between the fasteners.

61. The bone fastener construct of example 56 wherein the construct is applied in a lisfranc procedure.

62. A bone fastener comprising:
a first leg defining a longitudinal axis extending from a first leg leading end to a first leg trailing end, the first leg having a first connector and a second connector, the first and second connectors being spaced axially from one another;
a second leg defining a longitudinal axis extending from a second leg leading end to a second leg trailing end, the second leg having a receiver defining an elongate axial path;
a flexible member engaging the first connector of the first leg, extending to the second leg, engaging the receiver in sliding relationship with the elongate axial path, and extending back to the first leg and engaging the second connector.

63. The bone fastener of example 62 wherein the first leg longitudinal axis and second leg longitudinal axis define an angle between them, the legs being operable to vary the angle between the leg axes while maintaining equal tension in the flexible member.

64. The bone fastener of example 62 further comprising a tensioning mechanism operable to vary a length of the flexible member extending from the first leg.

65. The bone fastener of example 63 wherein the tensioning mechanism comprises a member threaded into the first leg and operable to draw the flexible member into the first leg.

66. A method of stabilizing a first bone portion relative to a second abutting bone portion, the method comprising:

providing a bone fastener having an insertion axis; a body having a body leading end and a body trailing end, the body leading end and the body trailing end being spaced from one another longitudinally relative to the insertion axis; a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being greater than the first trailing distance; and a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance;

inserting the bone fastener with the first leg in the first bone portion and the second leg in the second bone portion; and positioning the fastener with the trailing end of the body inside at least one of the first and second bone portions and below a cortical bone layer.

67. The method of example 66 wherein the trailing ends of the first and second legs extend longitudinally, relative to the insertion axis, proximally beyond the trailing end of the body 68. A method of stabilizing a first bone portion relative to a second abutting bone portion, the method comprising:

providing a bone fastener having an insertion axis; a body having a body leading end and a body trailing end, the body leading end and the body trailing end being spaced from one another longitudinally relative to the insertion axis; a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being greater than the first trailing distance; and a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance;

inserting the bone fastener with the first leg in the first bone portion and the second leg in the second bone portion; and positioning the fastener with no portion of the first leg trailing end, second leg trailing end, or body trailing end projecting out of the bone.

69. A bone joint implant comprising:
a longitudinal axis;

a spacer having a first bone engaging surface operable to engage a surface of a bone; and a first leg connected to the bone engaging surface, the first leg having a first elongate inboard surface facing the longitudinal axis and extending from a first leg leading end to a first leg trailing end, the first elongate inboard surface being spaced from the longitudinal axis a first leading distance at the leading end and the first elongate inboard surface being spaced from the longitudinal axis a first trailing distance at the first trailing end, the first leading distance being greater than the first trailing distance.

70. The bone joint implant of example 69 wherein the spacer further comprises an articulating surface opposite the bone engaging surface, the articulating surface having a shape and surface finish that facilitate articulation with an opposing bone or opposing articulating joint component.

71. The bone joint implant of example 69 wherein the first bone engaging surface includes a fixation feature projecting from the bone engaging surface.

72. The bone joint implant of example 71 wherein the fixation feature is selected from the group consisting of roughened textures, spikes, tabs, and posts.

73. The bone joint implant of example 69 wherein the first bone engaging surface is planar and parallel to the insertion axis.

74. The bone joint implant of example 69 wherein the first leg is moveably mounted for translation relative to the spacer parallel to the insertion axis.

75. The bone implant of example 74 wherein the first leg is provided as plurality of first legs, the plurality of first legs being interchangeably mountable relative to the spacer to provide a selectable size or shape of first leg.

76. The bone joint implant of example 1 further including a body between the spacer and the first leg, the body including an aperture operable to receive a transverse fixation member.

77. The bone joint implant of example 69 wherein the spacer is operable to space a femur and tibia at a knee joint, the spacer further comprising an articulating surface opposite the bone engaging surface, the articulating surface having a shape and surface finish that facilitate articulation with an opposing articulating surface of a femur or femoral implant.

78. The bone joint implant of example 69 wherein the spacer includes a second bone engaging surface opposite the first bone engaging surface and the implant further comprises:
a second leg connected to the second bone engaging surface, the second leg having a second elongate inboard surface facing the longitudinal axis and extending from a second leg leading end to a second leg trailing end, the second elongate inboard surface being spaced from the longitudinal axis a second leading distance at the leading end and the second elongate inboard surface being spaced from the longitudinal axis a second trailing distance at the second trailing end, the second leading distance being greater than or equal to the second trailing distance.

79. The bone joint implant of example 78 wherein the spacer is operable to space adjacent vertebral bodies of a human spine, the first leg being insertable into a first vertebral body to compress the first bone engaging surface against the first vertebral body and he second leg being insertable into a second vertebral body to compress the second bone engaging surface against the second vertebral body.

80. A bone joint system comprising:
a bone joint implant comprising:

a longitudinal axis;
a spacer having a first bone engaging surface operable to engage a surface of a bone; and
a first leg connected to the bone engaging surface, the first leg having a first elongate inboard surface facing the longitudinal axis and extending from a first leg leading end to a first leg trailing end, the first elongate inboard surface being spaced from the longitudinal axis a first leading distance at the leading end and the first elongate inboard surface being spaced from the longitudinal axis a first trailing distance at the first trailing end, the first leading distance being greater than the first trailing distance, the spacer first bone engaging surface and the first elongate inboard surface diverging to define a divergence angle; and
a hole forming guide comprising:
a guide body operable to guide a hole forming instrument along a guide axis;
a probe having a probe reference surface operable to engage a bone surface, the guide axis and probe reference surface diverging at an angle equal to the divergence angle.

81. A method of operating on a bone joint, the method comprising:
forming a first passage in a first bone adjacent to the joint;
engaging an implant with the first bone with a first bone engaging surface of the implant in engagement with an external surface of the first bone and a first leg of the implant inserted into the first passage;
advancing at least the first leg to cause compression of the first bone engaging surface against the external surface of the first bone.

82. The method of example 81 wherein the implant comprises:
a spacer defining the first bone engaging surface; and
the first leg is connected to the bone engaging surface, the first leg having a first elongate inboard surface facing the longitudinal axis and extending from a first leg leading end to a first leg trailing end, the first elongate inboard surface being spaced from the longitudinal axis a first leading distance at the leading end and the first elongate inboard surface being spaced from the longitudinal axis a first trailing distance at the first trailing end, the first leading distance being greater than the first trailing distance, the spacer first bone engaging surface and the first elongate inboard surface diverging to define a divergence angle.

83. The method of example 82 wherein the step of advancing at least the first leg into the first passage comprises advancing the spacer and the leg together to cause increasing compression.

84. The method of example 82 wherein the first leg is mounted for translation relative to the spacer, the step of engaging an implant with the first bone comprising positioning the spacer on the first bone at a desired location on the surface of the first bone and the step of advancing the first leg comprising advancing the first leg without changing the position of the spacer on the first bone.

85. The method of example 84 wherein the first bone engaging surface includes a fixation feature projecting from the first bone engaging surface, the method comprising first engaging the first bone engaging surface with the first bone in a first direction transverse to the first bone engaging surface and then advancing the first leg in a second direction transverse to the first direction.

86. The method of example 81 wherein the spacer comprises a tibial knee component and is operable to space a tibia and a femur at a knee joint, the first leg being operable to compress the spacer against the end of the tibia when the first leg is advanced into the tibia.

87. The method of example 82 wherein the spacer includes a second bone engaging surface opposite the first bone engaging surface and the implant further comprises a second leg connected to the second bone engaging surface, the second leg having a second elongate inboard surface facing the longitudinal axis and extending from a second leg leading end to a second leg trailing end, the second elongate inboard surface being spaced from the longitudinal axis a second leading distance at the leading end and the second elongate inboard surface being spaced from the longitudinal axis a second trailing distance at the second trailing end, the second leading distance being greater than or equal to the second trailing distance, the method further comprising:
forming a second passage in a second bone adjacent to the joint;
engaging the implant with the second bone with the second bone engaging surface of the implant in engagement with an external surface of the second bone and the second leg of the implant inserted into the second passage;
advancing the second leg to cause compression of the second bone engaging surface against the external surface of the second bone.

88. The method of example 87 wherein the spacer comprises a spinal disc implant and is operable to space first and second vertebral bodies of the spine, the first leg being operable to compress the spacer against the end of the first vertebral body when the when the first leg is advanced into the first vertebral body and the second leg being operable to compress the spacer against the end of second vertebral body when the second leg is advanced into the second vertebral body.

What is claimed is:

1. A bone fastener comprising:
an insertion axis;
a body with a generally planar configuration having opposed planar sides spaced apart a body thickness, the body extending between a distal body leading end and a proximal body trailing end, the body leading end and the body trailing end being spaced from one another longitudinally relative to the insertion axis, the opposed planar sides converging toward the body trailing end to define a trailing edge having a trailing edge thickness less than the body thickness;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being greater than the first trailing distance; and
a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance;

wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

2. The bone fastener of claim 1 wherein the body has a proximal body leading end and a distal body trailing end, the body leading end and the body trailing end being spaced from one another longitudinally relative to the insertion axis.

3. The bone fastener of claim 2 wherein the trailing end of each of the first and second legs extends proximally beyond the trailing edge of the body.

4. The bone fastener of claim 2 further comprising an aperture through the body, the aperture having a length and a width, the aperture length being greater than the aperture width, the aperture length being oriented transverse to the insertion axis.

5. A bone fastener construct stabilizing a first bone portion relative to a second abutting bone portion, the construct comprising:
an insertion axis along which the fastener moves as it is inserted into or removed from a bone;
a body and an aperture through the body, the aperture having a length and a width, the aperture length being greater than the aperture width, the aperture length being oriented transverse to the insertion axis;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and
a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance, wherein at least part of the first elongate inboard surface diverges from at least part of the second elongate inboard surface; and
an elongate fixation member positioned within the aperture and engaging at least one of the first and second bone portions.

6. The bone fastener construct of claim 5 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

7. The bone fastener construct of claim 5 wherein the trailing end of each of the first and second legs extends beyond the trailing edge of the body.

8. The bone fastener construct of claim 5 wherein the elongate fixation member engages both the first and second bone portions.

9. The bone fastener construct of claim 5 further comprising a guide having a guide axis, the guide being mounted to the fastener in rotating relationship, the guide being rotatable between a plurality of positions in which the guide axis intersects the aperture.

10. The bone fastener construct of claim 9 wherein the aperture defines a central axis parallel to the insertion axis, the guide being mounted for rotation about the central axis between a plurality of rotated positions, the guide axis intersecting the central axis in each of the plurality of rotated positions.

11. The bone fastener construct of claim 9 further comprising an elongate fixation member having a longitudinal axis and a width measured normal to the longitudinal axis, wherein the guide and fastener define at least one stop that limits the rotation of the guide relative to the fastener in at least one direction to an included angle between the guide axis and the aperture having a value corresponding to a projected length of the aperture along the guide axis equal to or greater than the width of the fixation member.

12. A bone fastener construct stabilizing a first bone portion relative to a second abutting bone portion, the construct comprising:
an insertion axis along which the fastener moves as it is inserted into or removed from a bone;
a body and an aperture through the body, the aperture having a length and a width, the aperture length being greater than the aperture width, the aperture length being oriented transverse to the insertion axis;
a first leg connected to the body, the first leg having a first elongate inboard surface facing the insertion axis and extending from a first leg leading end to a first leg trailing end, the first elongate inboard surface being spaced from the insertion axis a first leading distance at the leading end and the first elongate inboard surface being spaced from the insertion axis a first trailing distance at the trailing end, the first leading distance being equal to or greater than the first trailing distance; and
a second leg connected to the body, the second leg having a second elongate inboard surface facing the insertion axis and extending from a second leg leading end to a second leg trailing end, the second elongate inboard surface being spaced from the insertion axis a second leading distance at the leading end and the second elongate inboard surface being spaced from the insertion axis a second trailing distance at the trailing end, the second leading distance being equal to or greater than the second trailing distance, wherein at least part of the first elongate inboard surface diverges from at least part of the second elongate inboard surface; and
a guide having a guide axis, the guide being mounted to the fastener in rotating relationship, the guide being rotatable between a plurality of positions in which the guide axis intersects the aperture.

13. The bone fastener construct of claim 12 wherein the first leg has a first elongate outboard surface facing away from the insertion axis and extending at least half of the distance from the first leg leading end to the first leg trailing end and the second leg has a second elongate outboard surface facing away from the insertion axis and extending at least half of the distance from the first leg leading end to the first leg trailing end, the first and second elongate outboard surfaces each being parallel to the insertion axis.

14. The bone fastener construct of claim 12 wherein the trailing end of each of the first and second legs extends beyond the trailing edge of the body.

15. The bone fastener construct of claim 12 further comprising an elongate fixation member positioned within the aperture and engaging at least one of the first and second bone portions.

16. The bone fastener construct of claim 15 wherein the elongate fixation member engages both the first and second bone portions.

17. The bone fastener construct of claim 12 wherein the aperture defines a central axis parallel to the insertion axis, the guide being mounted for rotation about the central axis between a plurality of rotated positions, the guide axis intersecting the central axis in each of the plurality of rotated positions.

18. The bone fastener construct of claim 12 further comprising an elongate fixation member having a longitudinal axis and a width measured normal to the longitudinal axis, wherein the guide and fastener define at least one stop that limits the rotation of the guide relative to the fastener in at least one direction to an included angle between the guide axis and the aperture having a value corresponding to a projected length of the aperture along the guide axis equal to or greater than the width of the fixation member.

* * * * *